(12) United States Patent
Ishiwata

(10) Patent No.: US 11,596,505 B2
(45) Date of Patent: Mar. 7, 2023

(54) BIOLOGICAL TISSUE ROOTAGE FACE, IMPLANT, METHOD FOR FORMING BIOLOGICAL TISSUE ROOTAGE FACE, AND METHOD FOR PRODUCING IMPLANT

(71) Applicant: NANTOH. CO., LTD, Numazu (JP)

(72) Inventor: Teruo Ishiwata, Numazu (JP)

(73) Assignee: NANTOH. CO., LTD, Numazu (JP)

(*) Notice: Subject to any disclaimer, the term of this patent is extended or adjusted under 35 U.S.C. 154(b) by 399 days.

(21) Appl. No.: 16/912,083

(22) Filed: Jun. 25, 2020

(65) Prior Publication Data

US 2020/0345465 A1    Nov. 5, 2020

Related U.S. Application Data

(62) Division of application No. 16/339,571, filed as application No. PCT/JP2017/040076 on Nov. 7, 2017, now Pat. No. 11,051,915.

(51) Int. Cl.
*A61C 13/00* (2006.01)
*A61C 8/02* (2006.01)
(Continued)

(52) U.S. Cl.
CPC ........ *A61C 13/0018* (2013.01); *A61C 8/0006* (2013.01); *A61C 8/0012* (2013.01);
(Continued)

(58) Field of Classification Search
CPC .............. A61C 13/0018; A61C 8/0006; A61C 2008/0046
(Continued)

(56) References Cited

U.S. PATENT DOCUMENTS 5,310,343 A     5/1994  Hasegawa et al.
2001/0039454 A1 11/2001 Ricci et al.
(Continued)

FOREIGN PATENT DOCUMENTS

JP    2007-525280 A    9/2007
JP    2010-5379 A      1/2010
(Continued)

OTHER PUBLICATIONS

International Search Report dated Jan. 9, 2018, issued in counterpart application No. PCT/JP2017/040076, w/English translation. (5 pages).
(Continued)

*Primary Examiner* — Nicholas D Lucchesi
(74) *Attorney, Agent, or Firm* — WHDA, LLP

(57) ABSTRACT

A biological tissue rootage face (30) capable of closely bonding to a biological tissue (H, S) is composed of a biocompatible material and has numerous fingertip-shaped microvilli (41). The microvilli (41) have tip diameters in the order of nanometers. An implant (1) has the biological tissue rootage face (30) on a surface (11, 24) configured to root into a biological tissue (H, S). In a method for forming the biological tissue rootage face (30), a surface of a biocompatible material is subjected to laser nonthermal processing carried out by emitting a laser beam in air, to form numerous fingertip-shaped microvilli (41). The laser beam is a laser beam of an ultrashort pulse laser.

12 Claims, 19 Drawing Sheets

(51) Int. Cl.
  *A61C 8/00* (2006.01)
  *A61F 2/30* (2006.01)
  *A61F 2/32* (2006.01)

(52) U.S. Cl.
  CPC ........ *A61C 8/0022* (2013.01); *A61F 2/30767* (2013.01); *A61F 2/32* (2013.01); *A61F 2002/3097* (2013.01)

(58) Field of Classification Search
  USPC ...................................................... 433/201.1
  See application file for complete search history.

(56) References Cited

U.S. PATENT DOCUMENTS

| | | | |
|---|---|---|---|
| 2005/0119758 | A1 | 6/2005 | Alexander et al. |
| 2010/0173264 | A1 | 7/2010 | Fredriksson et al. |
| 2011/0136078 | A1 | 6/2011 | Ishiwata |
| 2020/0253739 | A1* | 8/2020 | Ishiwata .................. A61F 2/34 |
| 2021/0145553 | A1* | 5/2021 | Itakura ................ B23K 26/3584 |
| 2022/0151745 | A1* | 5/2022 | Mercelis ............ A61C 13/0018 |

FOREIGN PATENT DOCUMENTS

| | | | |
|---|---|---|---|
| JP | 2010-194170 | A | 9/2010 |
| JP | 2010-227551 | A | 10/2010 |
| JP | 2011-509098 | A | 3/2011 |
| JP | 2011-527917 | A | 11/2011 |
| JP | 2012-521232 | A | 9/2012 |
| JP | 2014-124500 | A | 7/2014 |
| JP | 2015-518738 | A | 7/2015 |
| JP | 2016-151 | A | 1/2016 |
| WO | 01/58374 | A2 | 8/2001 |
| WO | 01/58374 | A3 | 8/2001 |
| WO | 2004/098442 | A1 | 11/2004 |
| WO | 2010/006740 | A2 | 1/2010 |
| WO | 2010/108794 | A1 | 9/2010 |
| WO | 2013/167417 | A1 | 11/2013 |
| WO | 2014/103653 | A1 | 7/2014 |

OTHER PUBLICATIONS

Shinonaga et al., "Cell Spreading on titanium dioxide film formed and modified with aerosol beam and femtosecond laser", Applied Surface Science, Elsevier B.V., Jan. 1, 2014, vol. 288, pp. 649-653, cited in ISR (5 pages).

Shinonaga et al., "Creation of New Functional Biomaterials by Periodic Nanostructures Formation with Femtosecond Laser", Journal of the Japan Society for Precision Engineering, Japan, The—Japan Society for Precision Engineering, Aug. 5, 2015, vol. 81, No. 8, pp. 726-730, w/English translation, cited in ISR (11 pages).

Shinonaga, "Research on surface structure control of titanium material by short-pulse-laser exposure for improvement in biocompatible" Osaka University Doctoral dissertation, Japan, Shinonaga, Mar. 25, 2014, shell No. 17169, pp. 4-49 , w/English translation (187 pages).

Yoshinari, "Implant material and its surface: Part 4. Future Implants", Dental academic report, Japan, Tokyo Dental College Society, Aug. 30, 2003, vols. 103, No. 8, pp. 637-649, w/English translation (23 Pages).

Yoshinari et al., "Effects of multigrooved surfaces on fibroblast behavior", Journal of Biomedical Materials Research, USA, John wiley & Sons,Jun. 1, 2003, vol. 65A, Issue 3, pp. 359-368 (10 pages).

Office Action dated Jul. 30, 2019, issued in counterpart JP Application No. JP2019-122229, with English translation. (10 pages).

Delgado-Ruiz, R.A., "Femtosecond laser microstructuring of zirconia dental implants", Journal of Biomedical Materials Research B: Applied Biomaterials, Jan. 2011, vol. 96B, Issue 1, pp. 91-100; Cited in the AU Office Action dated Jan. 2, 2020. (10 pages).

Office Action dated Jan. 2, 2020, issued in counterpart AU Application No. 2017356025. (5 pages).

Extended (Supplementary) European Search Report dated May 15, 2020, issued in counterpart EP application No. 17868814.9. (23 pages).

Vorobyev et al., "Femtosecond laser structuring of titanium implants", Applied Surface Science, vol. 253, No. 17, May 24, 2007, pp. 7272-7280, cited in Extended European Search Report dated May 15, 2020. (9 pages).

* cited by examiner (a)

(b)

(a)

(b)

(c)

(d)

(e)

(f)

(a)

(b)

(c)

(d)

(e)

(f)

(a)

(b)

(c)

(a)

(b)

(c)

(a)

(b)

(a)

(b)

(a)

(b)

(c)

(d)

(e)

(a)

51

(b)

51

(c)

51

(d)  51

(e)  51

(a) 131(115)

(b) 131

(c) 131
141

(d)

(e)

(a)

(b)

(c)

(d)

BIOLOGICAL TISSUE ROOTAGE FACE, IMPLANT, METHOD FOR FORMING BIOLOGICAL TISSUE ROOTAGE FACE, AND METHOD FOR PRODUCING IMPLANT

This application is a Divisional of copending U.S. application Ser. No. 16/339,571, filed on Apr. 4, 2019, which is a 371 of International Application No. PCT/JP2017/040076, filed on Nov. 7, 2017, which claims the benefit of priority from the prior Japanese Patent Application No. 2016-219467, filed on Nov. 10, 2016, the entire contents of all of which are incorporated herein by references.

TECHNICAL FIELD

The present invention relates to a biological tissue rootage face, an implant, a method for forming the biological tissue rootage face, and a method for producing the implant.

BACKGROUND ART

Implants for body implantation have attracted attention. Implants include dental implants, artificial joints, artificial bones, and the like.

The dental implants are formed of a biocompatible material such as a biocompatible metallic material or a biocompatible ceramic material. The biocompatible metallic materials include titanium, a titanium alloy, a cobalt-chromium alloy and the like. The biocompatible ceramic materials include alumina, zirconia and the like.

A hip prosthesis, an artificial bone and the like are formed of a biocompatible metallic material and a biocompatible ceramic material, as well as a biocompatible resin material.

An outer surface of the implant closely bonds to a bone (hard tissue). The outer surface of the implant is roughened (porosification, etc.), so that bone ingrowth is enhanced, and high osseointegration can be obtained.

A resin implants can be exemplified by an implant prepared by coating a resin surface with a metal or a ceramic and roughening this coating.

FIG. 19 presents images (4 items) of outer surfaces of conventional titanium fixtures taken by SEM (magnification: 2,000 times). These outer surfaces are roughened (porosified) by etching treatment with hydrochloric acid or the like, or blasting treatment.

PRIOR ART DOCUMENTS

Patent Documents

Patent Document 1: Japanese Patent Application Laid-Open No. 2010-5379

SUMMARY OF INVENTION

Problem to be Solved

Even when an outer surface of an implant is roughened, it takes several weeks to several months for the implant to be osteointegrated. If excessive force is applied to the implant during this period, osseointegration becomes difficult, e.g. the surrounding bones or the like are damaged, or osseointegration is delayed. Thus, it is necessary to further improve the osseointegration of the implant (bondability to hard tissues).

Since the implant is closely bonded not only to a bone but also to mucosal tissues (soft tissues) surrounding the bone, the conglutination property (affinity) with the soft tissues is also important. When adhesion of the dental implant with a gingiva is insufficient, the gingiva has inflammation, and the gingiva (gum) may be contracted, or an alveolar bone may be reduced (bone resorption). For this reason, conglutination property of the dental implant with the gingiva (conglutination property with soft tissues) should be improved to prevent (block) bacterial invasion.

Implants require improvement of the ability of rooting into biological tissues (bondability with hard tissues, and conglutination property with soft tissues) and acceleration of biological tissue fusion.

An object of the present invention is to provide a biological tissue rootage face capable of improving the ability of rooting into biological tissues, an implant, a method for forming the biological tissue rootage face, and a method for producing the implant.

Solution to Problem

A first embodiment of a biological tissue rootage face according to the present invention is characterized in that the biological tissue rootage face is capable of rooting into a biological tissue, is composed of a biocompatible material and has numerous fingertip-shaped microvilli.

A second embodiment of the biological tissue rootage face according to the present invention is characterized in that, in the first embodiment, the microvilli have tip diameters in the order of nanometers.

A third embodiment of the biological tissue rootage face according to the present invention is characterized in that, in the second embodiment, the tip diameters are 50 nm or more and less than 500 nm.

A fourth embodiment of the biological tissue rootage face according to the present invention is characterized in that, in any one of the first to third embodiments, a size of a three-dimensional surface roughness Sa is in the order of nanometers.

A fifth embodiment of the biological tissue rootage face according to the present invention is characterized in that, in any one of the first to fourth embodiments, a developed area ratio Sdr of an interface is 0.1 or more and 2.0 or less.

A sixth embodiment of the biological tissue rootage face according to the present invention is characterized in that, in any one of the first to fifth embodiments, the biological tissue rootage face has a plurality of first grooves having widths of 1 μm or more and 50 μm or less.

A seventh embodiment of the biological tissue rootage face according to the present invention is characterized in that, in the sixth embodiment, the first grooves have depths of 1 μm or more and 20 μm or less.

An eighth embodiment of the biological tissue rootage face according to the present invention is characterized in that, in the sixth or seventh embodiment, the first grooves are arranged in parallel or in a lattice pattern.

A ninth embodiment of the biological tissue rootage face according to the present invention is characterized in that, in any one of the first to eighth embodiments, the biological tissue rootage face has a plurality of second grooves having widths of 10 μm or more and 500 μm or less.

A tenth embodiment of the biological tissue rootage face according to the present invention is characterized in that, in the ninth embodiment, the second grooves have depths of 5 μm or more and 500 μm or less.

An eleventh embodiment of the biological tissue rootage face according to the present invention is characterized in that, in the ninth or tenth embodiment, the second grooves are arranged in parallel or in a lattice pattern.

A twelfth embodiment of the biological tissue rootage face according to the present invention is characterized in that, in any one of the first to eleventh embodiments, the biocompatible material is a biocompatible ceramic material.

A thirteenth embodiment of the biological tissue rootage face according to the present invention is characterized in that, in the twelfth embodiment, the biocompatible ceramic material contains zirconia.

A fourteenth embodiment of the biological tissue rootage face according to the present invention is characterized in that, in any one of the first to the eleventh embodiments, the biocompatible material is a biocompatible metallic material.

A fifteenth embodiment of the biological tissue rootage face according to the present invention is characterized in that, in the fourteenth embodiment, the biocompatible material contains titanium, a titanium alloy, or a cobalt-chromium alloy.

A sixteenth embodiment of the biological tissue rootage face according to the present invention is characterized in that, in any one of the first to eleventh embodiments, the biocompatible material is a biocompatible resin material.

A seventeenth embodiment of the biological tissue rootage face according to the present invention is characterized in that, in the sixteenth embodiment, the biocompatible resin material contains a polyetheretherketone resin.

A first embodiment of the implant according to the present invention is characterized in that the implant is capable of rooting into a biological tissue and has any one of the first to seventeenth embodiments of the biological tissue rootage face according to the present invention on a surface configured to root into a biological tissue.

A second embodiment of the implant according to the present invention is characterized in that, in the first embodiment, the implant is a screw-type fixture of a dental implant and the biological tissue rootage face is provided on at least one of a screw face, a collar face and a tip face.

A third embodiment of the implant according to the present invention is characterized in that, in the first embodiment, the implant is a cylinder-type fixture of the dental implant and the biological tissue rootage face is provided on at least one of the tip face and an outer peripheral face.

A fourth embodiment of the implant according to the present invention is characterized in that, in the first embodiment, the implant is an abutment of the dental implant and the biological tissue rootage face is provided on a gingival margin face.

A fifth embodiment of the implant according to the present invention is characterized in that, in the first embodiment, the implant is a stem of a hip prosthesis and the biological tissue rootage face is provided on a surface of a site implanted in a femur.

A first embodiment of a method for forming the biological tissue rootage face according to the present invention is characterized in that the method is a method for forming the biological tissue rootage face capable of rooting into a biological tissue, wherein a surface of a biocompatible material is subjected to laser nonthermal processing carried out by emitting a laser beam in air, to form numerous fingertip-shaped microvilli.

A second embodiment of the method for forming the biological tissue rootage face according to the present invention is characterized in that, in the first embodiment, the laser beam is a laser beam of an ultrashort pulse laser.

A third embodiment of the method for forming the biological tissue rootage face according to the present invention is characterized in that, in the second embodiment, the laser beam is a laser beam of a picosecond laser or a femtosecond laser.

A fourth embodiment of the method for forming the biological tissue rootage face according to the present invention is characterized in that, in any one of the first to third embodiments, the microvilli have tip diameters in the order of nanometers.

A fifth embodiment of the method for forming the biological tissue rootage face according to the present invention is characterized in that, in any one of the first to fourth embodiments, a ceramic sintered compact composed of a biocompatible ceramic material is non-thermally processed with laser.

A sixth embodiment of the method for forming the biological tissue rootage face according to the present invention is characterized in that, in the fifth embodiment, the biocompatible ceramic material contains zirconia.

A seventh embodiment of the method for forming the biological tissue rootage face according to the present invention is characterized in that, in any one of the first to fourth embodiments, an acid-etched metallic workpiece composed of a biocompatible metallic material is non-thermally processed with laser.

An eighth embodiment of the method for forming the biological tissue rootage face according to the present invention is characterized in that, in the seventh embodiment, the biocompatible metallic material contains titanium, a titanium alloy, or a cobalt-chromium alloy.

A ninth embodiment of the method for forming the biological tissue rootage face according to the present invention is characterized in that, in any one of the first to fourth embodiments, a resin compact composed of a biocompatible resin material is non-thermally processed with laser.

A tenth embodiment of the method for forming the biological tissue rootage face according to the present invention is characterized in that, in the ninth embodiment, the biocompatible resin material contains a polyetheretherketone resin.

An eleventh embodiment of the method for forming the biological tissue rootage face according to the present invention is characterized in that, in any one of the first to tenth embodiments, a plurality of first grooves having widths of 1 μm to 50 μm and depths of 1 μm to 20 μm are formed by scanning the surface of the biocompatible material with the laser beam.

A twelfth embodiment of the method for forming the biological tissue rootage face according to the present invention is characterized in that, in the eleventh embodiment, the first grooves are arranged in parallel or in a lattice pattern by scanning the surface of the biocompatible material with the laser beam in a parallel direction or an intersecting direction.

A thirteenth embodiment of the method for forming the biological tissue rootage face according to the present invention is characterized in that, in any one of the first to twelfth embodiments, a plurality of second grooves having widths of 10 μm to 500 μm and depths of 5 μm to 500 μm are formed by scanning the surface of the biocompatible material with the laser beam.

A fourteenth embodiment of the method for forming the biological tissue rootage face according to the present invention is characterized in that, in the thirteenth embodiment, the second grooves are arranged in parallel or in a lattice pattern by scanning the surface of the biocompatible material with the laser beam in a parallel direction or an intersecting direction.

A first embodiment of a method for producing the implant according to the present invention is characterized in that the method is a method for producing the implant capable of rooting into a biological tissue, wherein a step of forming the surface capable of rooting to the biological tissue includes any embodiments of the first to fourteenth embodiments of the method for forming the biological tissue rootage face according to the present invention.

A second embodiment of the method for producing the implant according to the present invention is characterized in that, in the first embodiment, the implant is a fixture of a dental implant.

A third embodiment of the method for producing the implant according to the present invention is characterized in that, in the first embodiment, the implant is an abutment of the dental implant.

A fourth embodiment of the method for producing the implant according to the present invention is characterized in that, in the first embodiment, the implant is a stem of a hip prosthesis.

Effects of Invention

The biological tissue rootage face, the implant, the method for forming the biological tissue rootage face, and the method for producing the implant according to the present invention can improve the ability of rooting into the biological tissue.

DESCRIPTION OF EMBODIMENTS

Embodiments of the present invention will be explained with reference to the drawings. Each of sizes and the like in the following explanation is described as an example.

[Dental Implant 1, Fixture 10]

Figure 1:
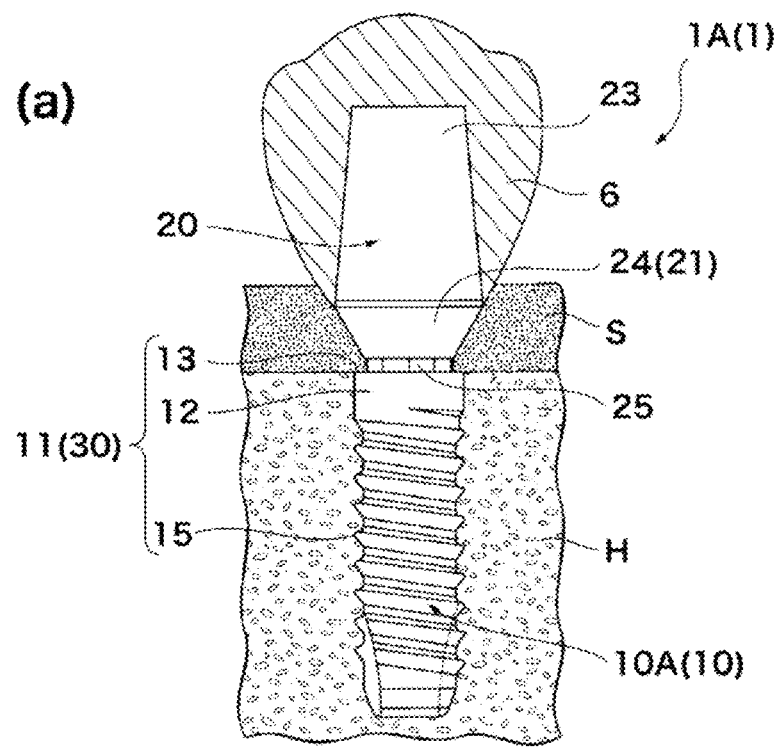
FIG. 1 presents drawings of a dental implant 1 according to the first embodiment of the present invention, including (a) a screw-type dental implant 1A and (b) a cylinder-type dental implant 1B.
Figure 1:
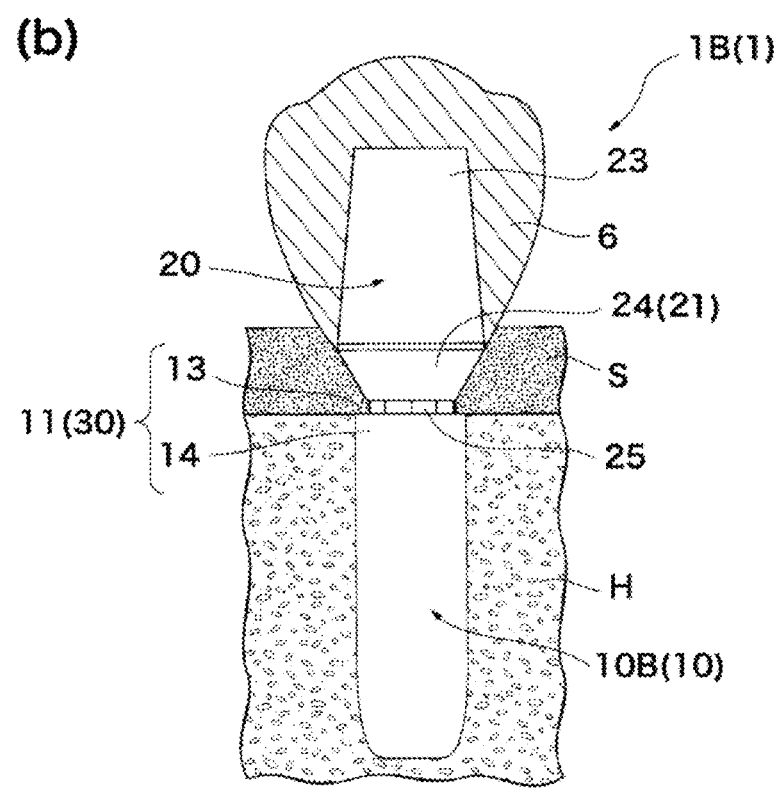

FIG. 1 presents drawings of a dental implant 1 according to the first embodiment of the present invention, including (a) a screw-type dental implant 1A and (b) a cylinder-type dental implant 1B.

The dental implant 1 is a zirconia implant. The dental implant 1 includes a screw-type dental implant 1A and a cylinder-type dental implant 1B.

The dental implant 1 comprises a fixture 10 fixed to an alveolar bone H (biological tissue, hard tissue), and an abutment 20 fitted into the fixture 10.

A crown 6 called an artificial crown is attached to the abutment 20. An end side of the abutment 20 opposite to the crown 6 is covered with a gum S (biological tissue, soft tissue).

A longitudinal direction (direction along the central axis) of the dental implant 1 is referred to as "vertical". In the vertical direction, a side of the crown 6 is referred to as a tip side. The tip is also referred to as a first end. In the vertical direction, a side of the fixture 10 is referred to as a root end side. The root end is also referred to as a second end.

A direction perpendicular to the vertical direction is referred to as "horizontal". A direction around the central axis of the dental implant 1 is referred to as a circumferential direction.

The fixture (implant) 10 is a shaft-shaped member having a central hole (not illustrated in the figures) and is formed of a ceramic (biocompatible material, biocompatible ceramic material) including zirconia.

The fixture 10 includes a screw-type fixture 10A having a male screw 15 formed on an outer surface 11, and a cylinder-type fixture 10B having no male screw 15. Between the screw-type fixture 10A and the cylinder-type fixture 10B, there is a difference only in the presence of the male screw 15.

The screw-type fixture 10A is screwed into a screw hole formed on the alveolar bone H, so that the fixture 10A is fixed to the alveolar bone H.

The cylinder-type fixture 10B is fitted into a circular hole formed on the alveolar bone H, so that the fixture 10B is fixed to the alveolar bone H.

A central hole is formed at the center of the tip face 13 of the fixture 10. The central hole is formed along the vertical direction.

The fixture 10 may have any shape (length, thickness, etc.). The fixture 10 may have no central hole.

[Biological Tissue Activation Surface 30]

The fixture 10 has a biological tissue rootage face 30 (biological tissue rootage faces 31 to 35). The biological tissue rootage face 30 is formed on the outer surface 11 of the fixture 10.

In the fixture 10A, the outer surface 11 includes the tip face 13, a collar face 12, and a screw face (male screw 15).

In the fixture 10B, the outer surface 11 includes the tip face 13 and an outer peripheral face 14.

The biological tissue rootage face 30 is excellent in bondability with the alveolar bone H and the conglutination property with the gum S. The biological tissue rootage face 30 has numerous microvilli 41 described later. The microvilli 41 are crowded. The biological tissue rootage face 30 is a face with dense microvilli.

The biological tissue rootage face 30 may have either or both of small grooves 43 and large grooves 45 described later in addition to the microvilli 41.

The fixture 10 is closely bonded to not only the alveolar bone H but also the mucosal tissues (soft tissues) surrounding the alveolar bone H. The tip face 13 is closely bonded to the gum S. Thus, the fixture 10 is also important for the conglutination property (affinity) with the soft tissue. If the conglutination property of the fixture 10 with the gum S is low, the gum S has inflammation, resulting in contraction of the gum S and reduction of the alveolar bone H (bone resorption). Thus, the conglutination property between the fixture 10 and the gums S (conglutination property with the soft tissues) should be improved to prevent (block) bacterial invasion.

The biological tissue rootage face 30 improves osseointegration and gum adhesion of the fixture 10 by the microvilli 41, the small grooves 43, and the large grooves 45. The biological tissue rootage face 30 improves the rooting ability of the fixture 10 into the biological tissue (bondability with hard tissues, and conglutination property with soft tissues) and accelerates the biological tissue fusion.

(Biological Tissue Rootage Face 31)

Figure 2:
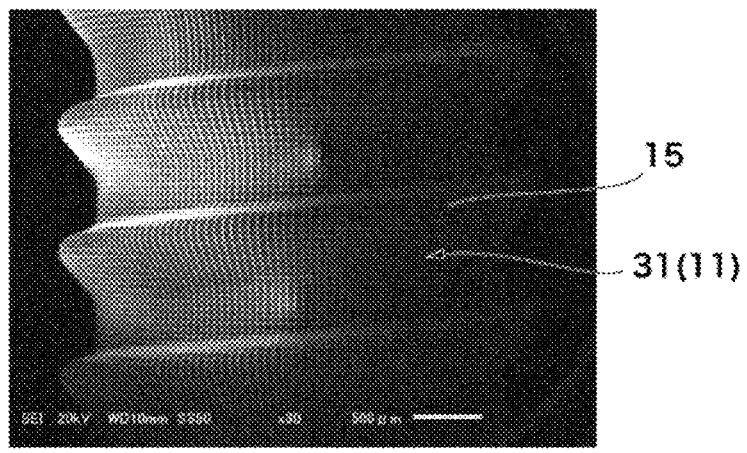
FIG. 2 presents images of a biological tissue rootage face 30 (biological tissue rootage face 31) according to the first embodiment of the present invention taken by SEM, including (a) an image at a magnification of 30 times, (b) an image at a magnification of 200 times, and (c) an image at a magnification of 500 times.
Figure 2:
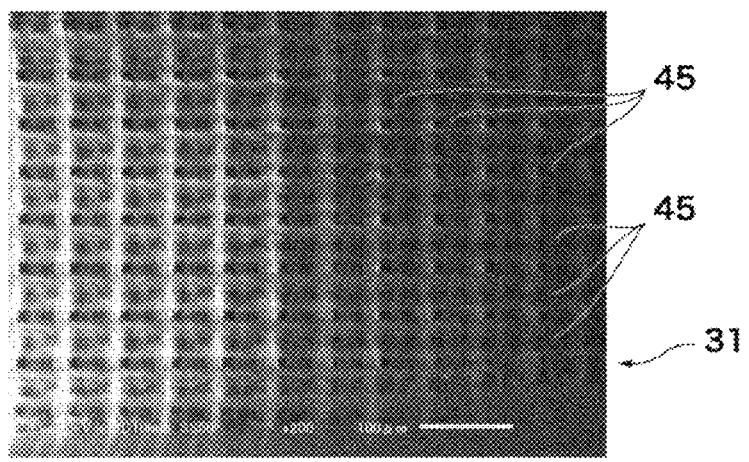
Figure 2:
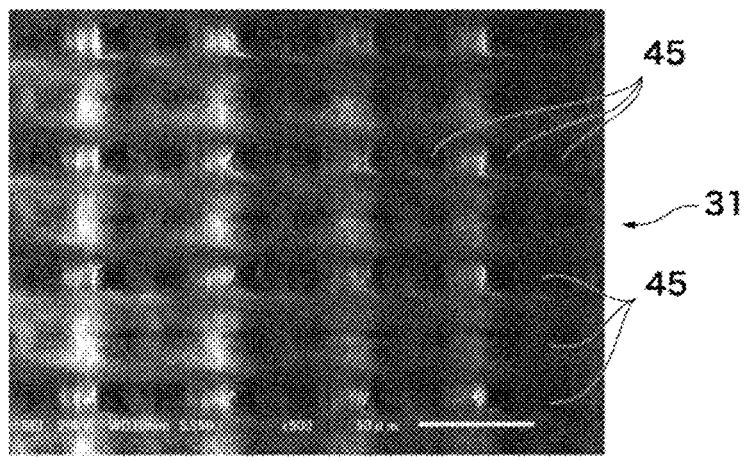
Figure 3:
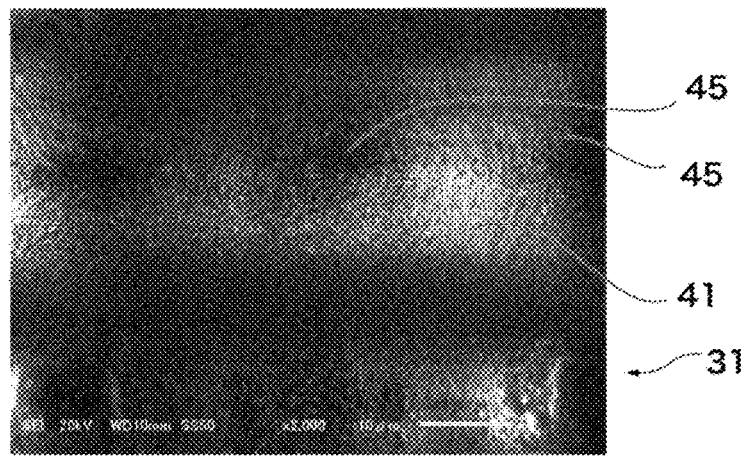
FIG. 3 presents images of the biological tissue rootage face 30 (biological tissue rootage face 31) according to the first embodiment of the present invention taken by SEM, including (d) an image at a magnification of 2,000 times, (e) an image at a magnification of 5,000 times, and (f) an image at a magnification of 10,000 times.
Figure 3:
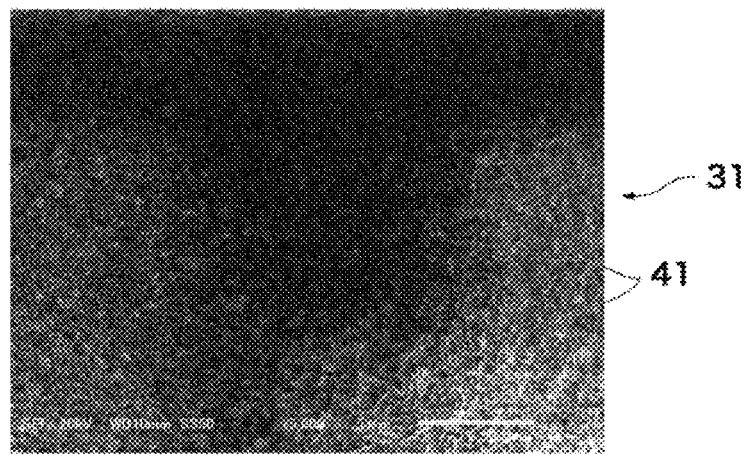
Figure 3:
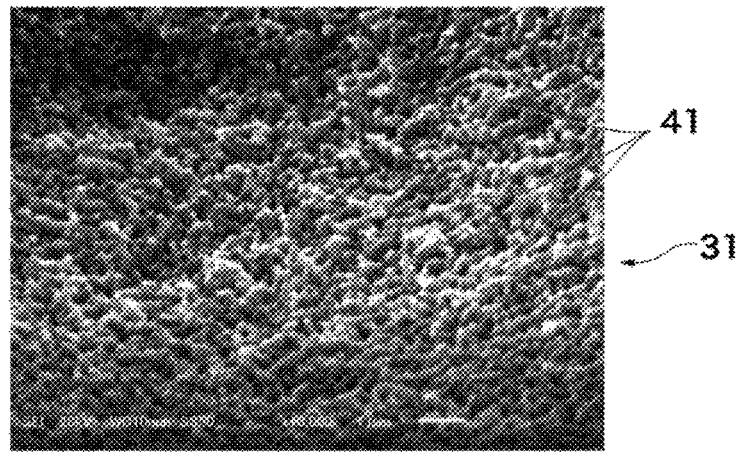

FIGS. 2 and 3 present images of the biological tissue rootage face 30 (biological tissue rootage face 31) according to the first embodiment of the present invention taken by SEM, including (a) an image at a magnification of 30 times, (b) an image at a magnification of 200 times, (c) an image at a magnification of 500 times, (d) an image at a magnification of 2,000 times, (e) an image at a magnification of 5,000 times, and (f) an image at a magnification of 10,000 times.

The biological tissue rootage face 31 is an example of the biological tissue rootage face 30 and is formed on the outer surface 11 of the fixture 10A.

The biological tissue rootage face 31 has numerous microvilli 41 having fingertip-shaped tips. The numerous microvilli 41 are densely arranged. The fingertip shape means a shape with a rounded tip (hemispherical shape) like a fingertip. The tip of the microvillus 41 is a hemispherical protrusion but is not pointed.

The microvillus 41 has a tip outer diameter (diameter) in the order of nanometers. The nanometer size is also referred to as "nanometer order", "nanometer scale", or "nanometer class" in some cases. The term "order of magnitude" in English is translated as "grade", "class", "scale", "digit" or the like in Japanese.

The tip diameter of the microvillus 41 is 1 nm or more and less than 1000 nm. The tip diameter of the microvillus 41 is e.g. 50 nm or more and less than 500 nm, and may also be e.g. 100 nm or more and less than 300 nm.

Also the biological tissue rootage face 31 has a three-dimensional surface roughness Sa in the order of nanometers (1 nm or more and less than 1000 nm) (arithmetic average height: ISO 25178). For example, the biological tissue rootage face 31 has a three-dimensional roughness Sa of 500 nm or more and less than 800 nm.

The biological tissue rootage face 31 has an interface developed area ratio Sdr (ISO 25178) of 0.1 or more and 2.0 or less. The biological tissue rootage face 31 has the interface developed area ratio Sdr of e.g. 0.5 or more and 1.0 or less.

The biological tissue rootage face 31 has a plurality of large grooves 45. The plurality of large grooves 45 are arranged so as to intersect with each other. The plurality of large grooves 45 are arranged in a lattice pattern. This is because egg-shaped osteoblasts of about 20 to 30 µm in size are securely fixed inside the large grooves 45.

The large grooves (second grooves) 57 have widths of 10 µm or more and 500 µm or less. The widths of the large grooves 45 are e.g. 20 µm or more and 100 µm or less, and may also be 30 μm or more and 50 μm or less. This is because the osteoblasts are prevented from spreading too much.

Depths of the large grooves 45 are 5 μm or more and 500 μm or less, and may also be e.g. 10 μm or more and 100 μm or less. This is because the osteoblasts are prevented from getting over the large grooves 45.

The large grooves 45 juxtaposed in a lengthwise direction and the large grooves 45 juxtaposed in a lateral direction (circumferential direction) intersect with each other. An intersection angle of the large grooves 45 may be any angle of 60° or larger.

(Biological Tissue Rootage Face 32)

Figure 4:
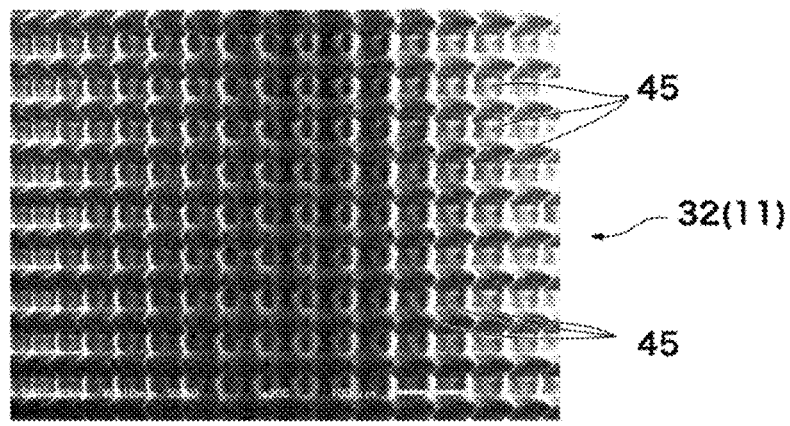
FIG. 4 presents images of the biological tissue rootage face 30 (biological tissue rootage face 32) according to the first embodiment of the present invention taken by SEM, including (a) an image at a magnification of 200 times, (b) an image at a magnification of 500 times, and (c) an image at a magnification of 2,000 times.
Figure 4:
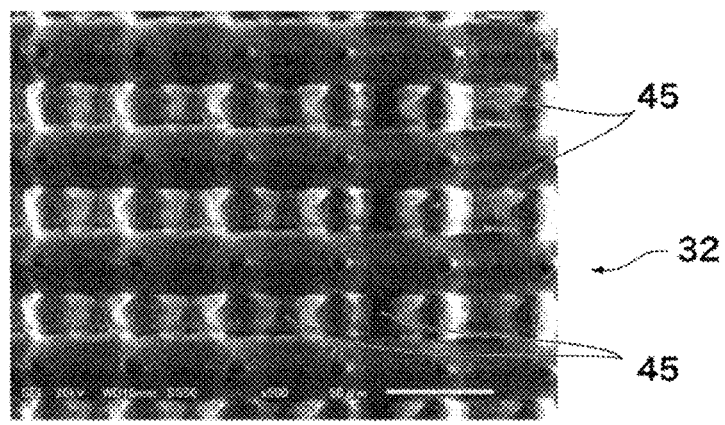
Figure 4:
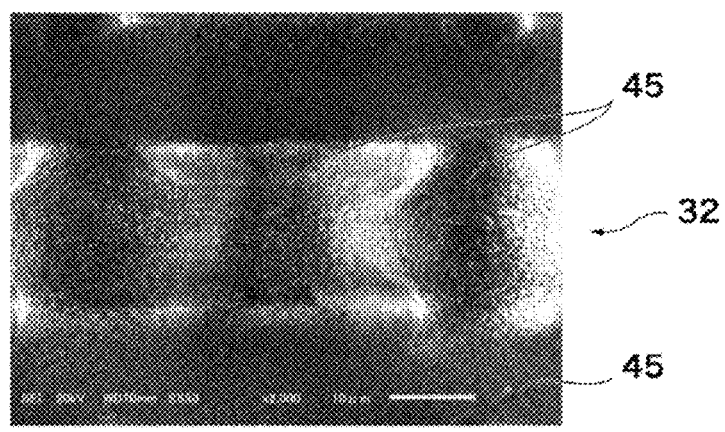
Figure 5:
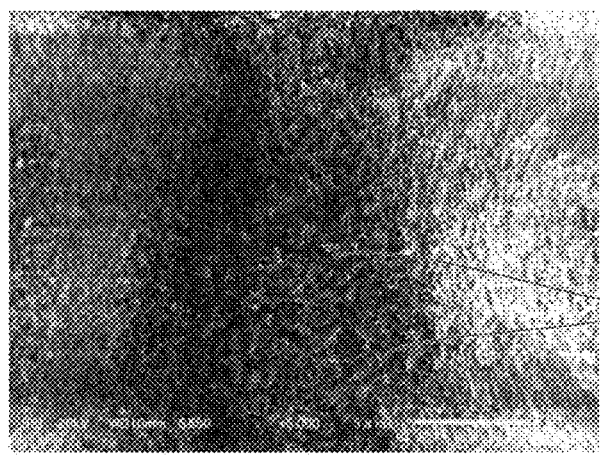
FIG. 5 presents images of the biological tissue rootage face 30 (biological tissue rootage face 32) according to the first embodiment of the present invention taken by SEM, including (d) an image at a magnification of 5,000 times, (e) an image at a magnification of 10,000 times, and (f) an image at a magnification of 20,000 times.
Figure 5:
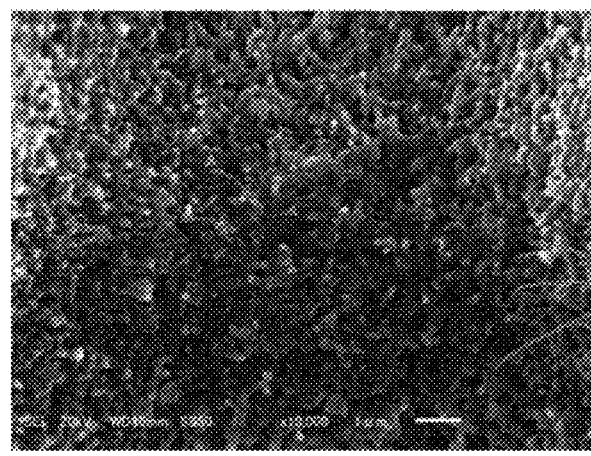
Figure 5:
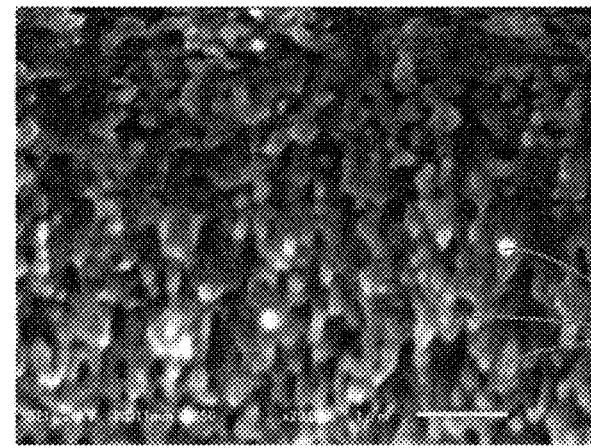

FIGS. 4 and 5 present images of a biological tissue rootage face 30 (biological tissue rootage face 32) according to the first embodiment of the present invention taken by SEM, including (a) an image at a magnification of 200 times, (b) an image at a magnification of 500 times, (c) an image at a magnification of 2,000 times, (d) an image at a magnification of 5,000 times, (e) an image at a magnification of 10,000 times, and (f) an image at a magnification of 20,000 times.

The biological tissue rootage face 32 is an example of the biological tissue rootage face 30 and is formed on the outer surface 11 of the fixture 10B.

The biological tissue rootage face 32 is formed in the same manner as for the biological tissue rootage face 31.

(Reference: Small Intestinal Villus and Microvillus)

Figure 6:
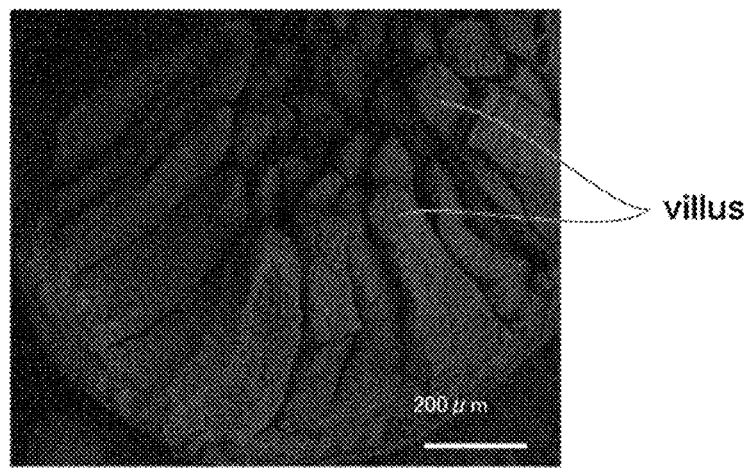
FIG. 6 presents referential images of a small intestinal surface taken by SEM, including (a) an image at a magnification of about 100 times, (b) an image at a magnification of about 5,000 times, and (c) an image at a magnification of about 10,000 times.
Figure 6:
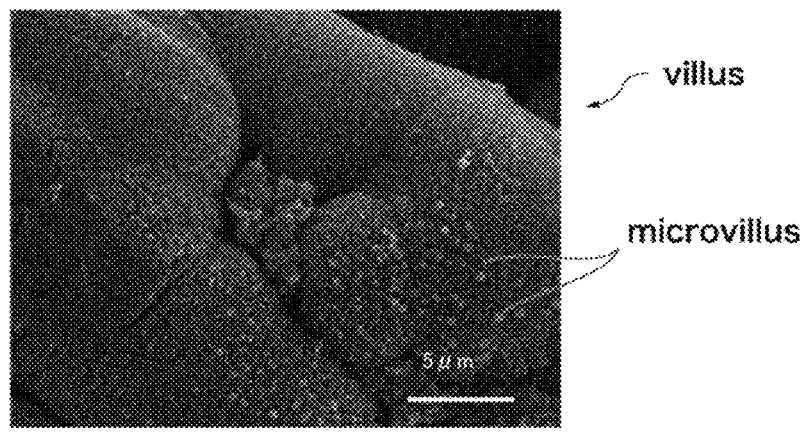
Figure 6:
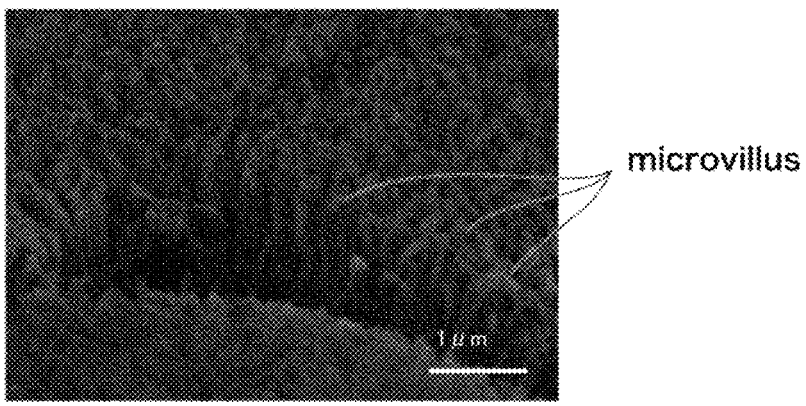

FIG. 6 presents referential images of a small intestinal surface taken by SEM, including (a) an image at a magnification of about 100 times, (b) an image at a magnification of about 5,000 times, and (c) an image at a magnification of about 10,000 times.

As shown in FIG. 6 (a), the small intestinal inner surface has numerous villi (villus). The villus refers to fine protrusions protruding from a surface of an organ, and exist in small intestine, placenta and the like.

As shown in FIGS. 6 (b) and 6 (c), in the surfaces of the villi, even more microvilli (microvillus) are densely present. The microvillus itself may also be referred to as soft hair or soft protrusion in some cases.

The tips of the villus and the microvillus are fingertip-shaped protrusions. The tip diameter of the microvillus is less than 1 μm. In the small intestine, placenta, or the like, the surface area is significantly increased by villi and microvilli, and absorption and bonding are efficiently and effectively performed.

The biological tissue rootage faces 31 and 32 have a structure similar to that of the inner surface of the small intestine or the like. The large grooves 45 are similar to the villi of the biological tissue, and the microvilli 41 are similar to the microvilli of the biological tissue.

For this reason, the biological tissue rootage face 31 has high bondability and conglutination property with the biological tissue (hard tissues such as bone, soft tissues such as mucosal tissue). The biological tissue rootage face 31 is considered to have an almost ideal shape as a surface configured to be closely bonded to biological tissues and root thereinto.

(Biological Tissue Rootage Face 33)

Figure 7:
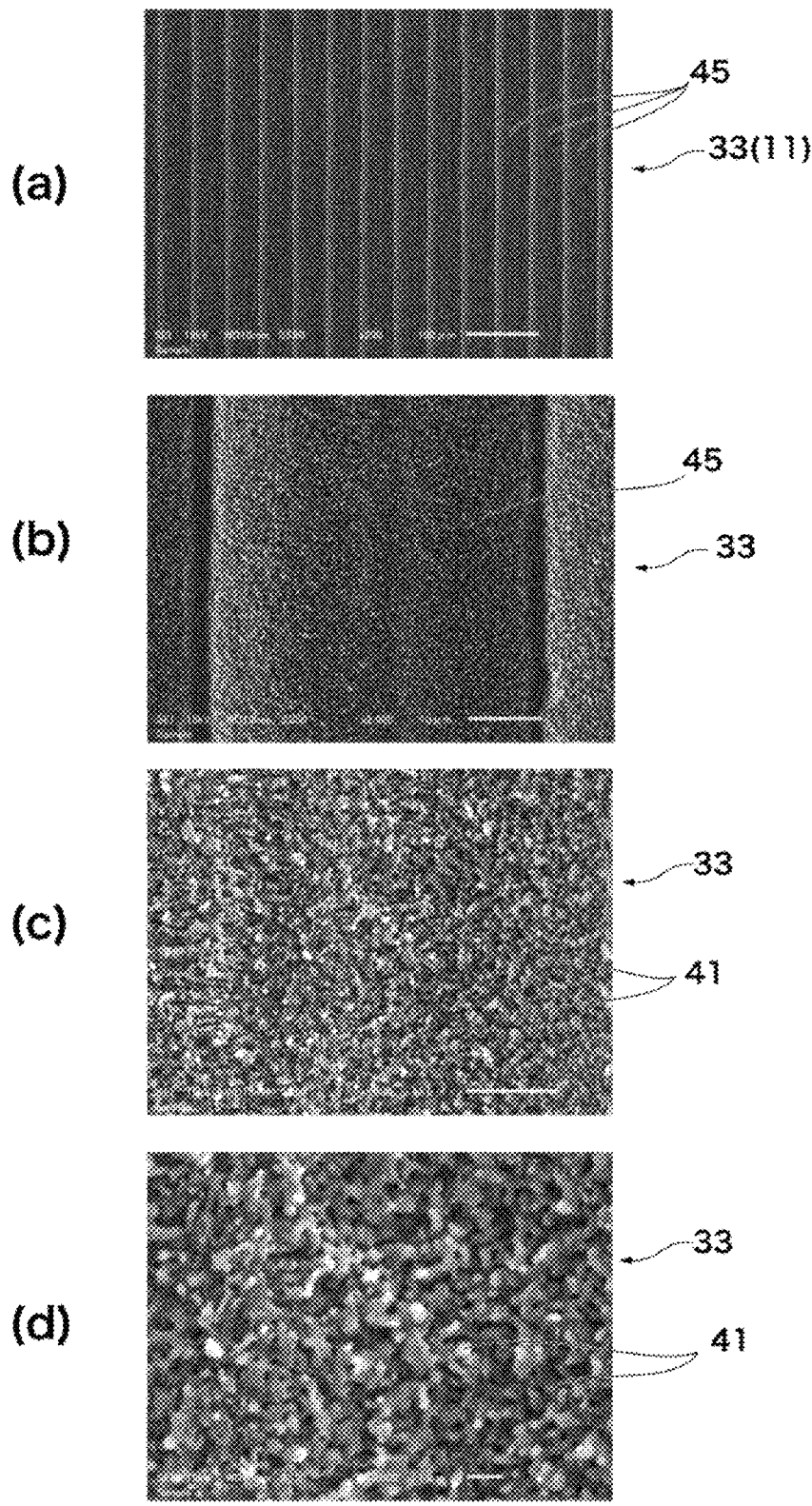
FIG. 7 presents images of a biological tissue rootage face 30 (biological tissue rootage face 33) according to the first embodiment of the present invention taken by SEM, including (a) an image at a magnification of 200 times, (b) an image at a magnification of 2,000 times, (c) an image at a magnification of 5,000 times, and (d) an image at a magnification of 10,000 times.

FIG. 7 presents images of a biological tissue rootage face 30 (biological tissue rootage face 33) according to the first embodiment of the present invention taken by SEM, including (a) an image at a magnification of 200 times, (b) an image at a magnification of 2,000 times, (c) an image at a magnification of 5,000 times, and (d) an image at a magnification of 10,000 times.

The biological tissue rootage face 33 is an example of the biological tissue rootage face 30 and is formed on the outer surface 11 of the fixture 10B.

Like the biological tissue rootage faces 31 and 32, the biological tissue rootage face 33 has numerous microvilli 41. The biological tissue rootage face 33 has the same three-dimensional roughness Sa and interface developed area ratio Sdr as those of the biological tissue rootage faces 31 and 32.

The biological tissue rootage face 33 has a plurality of large grooves 45 arranged in parallel. The shape and the like of the large groove 45 are as described above.

(Biological Tissue Rootage Face 34)

Figure 8:
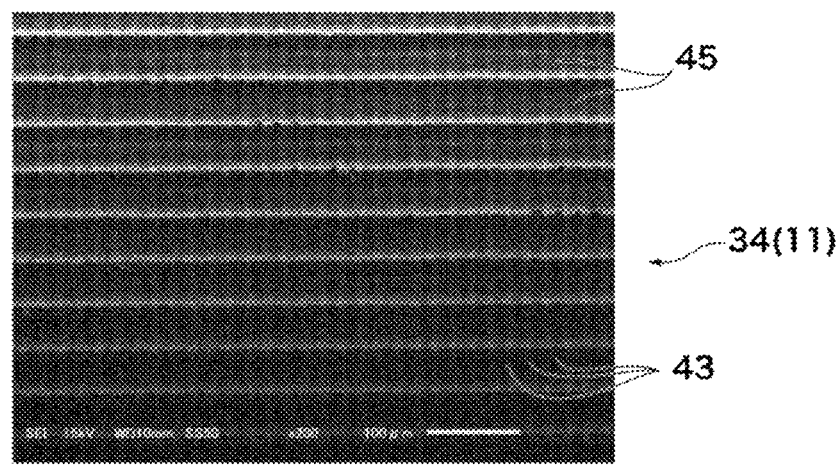
FIG. 8 presents images of a biological tissue rootage face 30 (biological tissue rootage face 34) according to the first embodiment of the present invention taken by SEM, including (a) an image at a magnification of 200 times, (b) an image at a magnification of 500 times, and (c) an image at a magnification of 10,000 times.
Figure 8:
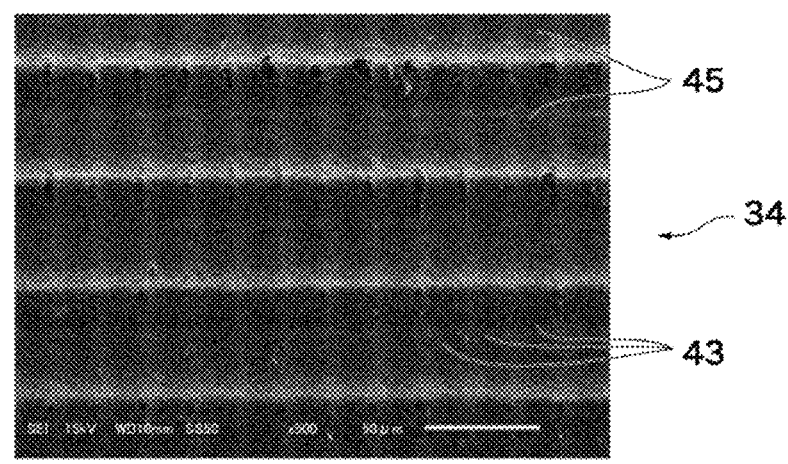
Figure 8:
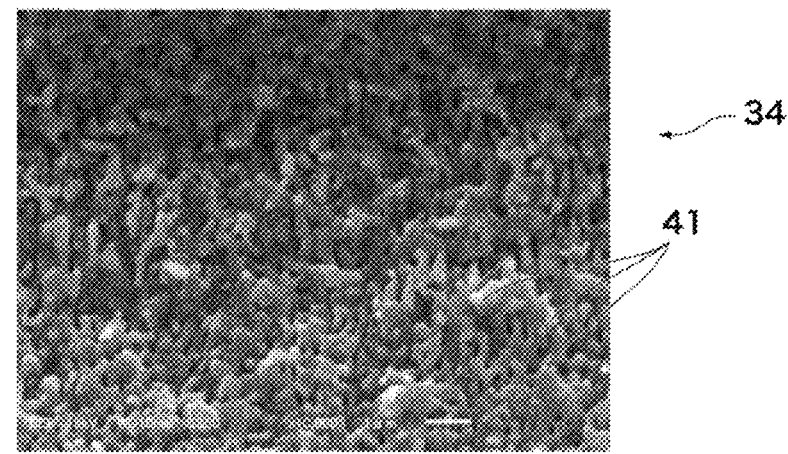

FIG. 8 presents images of a biological tissue rootage face 30 (biological tissue rootage face 34) according to the first embodiment of the present invention taken by SEM, including (a) an image at a magnification of 200 times, (b) an image at a magnification of 500 times, and (c) an image at a magnification of 10,000 times.

The biological tissue rootage face 34 is an example of the biological tissue rootage face 30 and is formed on the outer surface 11 of the fixture 10B.

Like the biological tissue rootage faces 31 to 33, the biological tissue rootage face 34 has numerous microvilli 41. The biological tissue rootage face 34 has the same three-dimensional roughness Sa and interface developed area ratio Sdr as those of the biological tissue rootage faces 31 to 33.

The biological tissue rootage face 34 has the plurality of small grooves 43 and large grooves 45. The plurality of small grooves 43 are arranged in parallel. The plurality of large grooves 45 are also arranged in parallel. The small grooves 43 and the large grooves 45 intersect each other in a lattice pattern. An intersection angle of the small grooves 43 and large grooves 45 may be any angle of 60° or larger.

The shape and the like of the large groove 45 are as described above.

The small grooves (first grooves) 43 have widths of 1 μm or more and 50 μm or less and are arranged in parallel. For example, the widths of the small grooves 43 are 1 μm or more and 20 μm or less, and may be e.g. 5 μm or more and 10 μm or less. Depths of the small grooves 43 are 1 μm or more and 20 μm or less, and may be e.g. 2 μm or more and 5 μm or less. This is because a mechanical stimulation (mechanical stress) is applied to osteoblasts.

(Biological Tissue Rootage Face 35)

Figure 9:
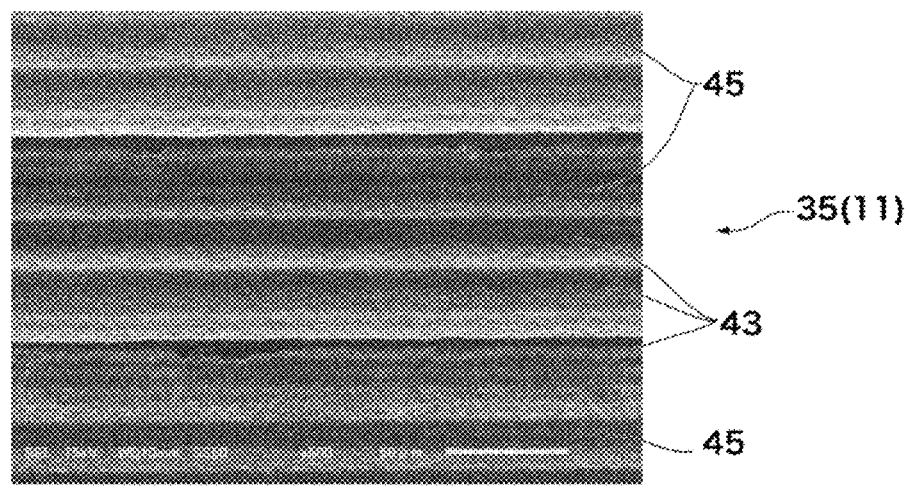
FIG. 9 presents images of a biological tissue rootage face 30 (biological tissue rootage face 35) according to the first embodiment of the present invention taken by SEM, including (a) an image at a magnification of 500 times, and (b) an image at a magnification of 10,000 times.
Figure 9:
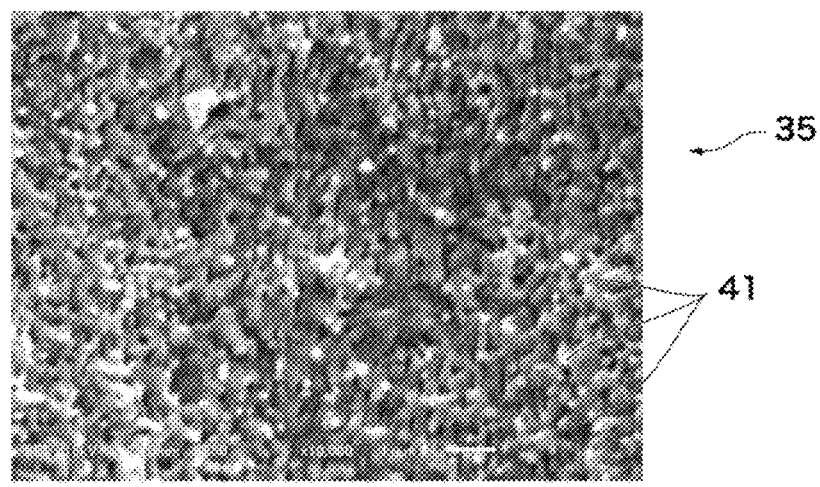

FIG. 9 presents images of a biological tissue rootage face 30 (biological tissue rootage face 35) according to the first embodiment of the present invention taken by SEM, including (a) an image at a magnification of 500 times, and (b) an image at a magnification of 10,000 times.

The biological tissue rootage face 35 is an example of the biological tissue rootage face 30 and is formed on the outer surface 11 of the fixture 10A.

Like the biological tissue rootage faces 31 to 34, the biological tissue rootage face 35 has numerous microvilli 41. The biological tissue rootage face 35 has the same three-dimensional roughness Sa and interface developed area ratio Sdr as those of the biological tissue rootage faces 31 to 34.

The biological tissue rootage face 35 has the plurality of small grooves 43 arranged in parallel and the plurality of large grooves 45 arranged in parallel. The small grooves 43 and the large grooves 45 are arranged in parallel. The plurality of small grooves 43 are arranged (superposed) inside the large grooves 45. The small grooves 43 and the large grooves 45 are parallel to each other. An intersection angle of the small grooves 43 and large grooves 45 may be any angle of 30° or smaller.

The shapes and the like of the small grooves 43 and the large grooves 45 are as described above.

Figure 19:
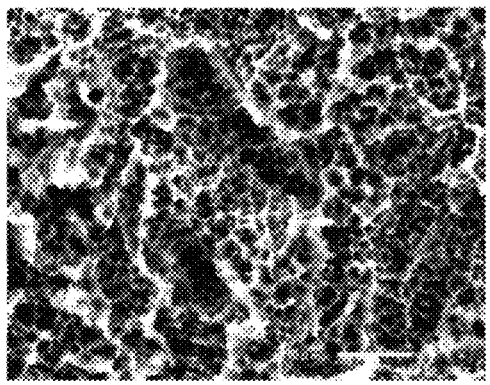
FIG. 19 presents images of outer surfaces of conventional titanium fixtures taken by SEM (magnification: 2,000 times), including (a) a product manufactured by Company A, (b) a product manufactured by Company B, (c) a product manufactured by Company C, and (d) a product manufactured by Company D.
Figure 19:
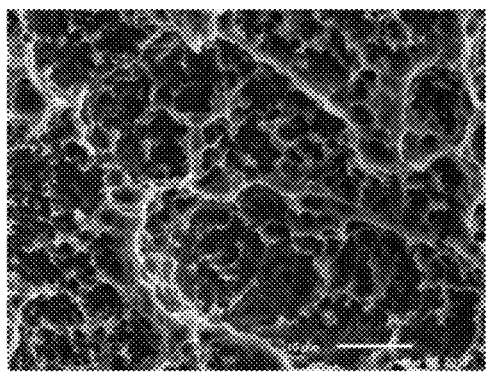
Figure 19:
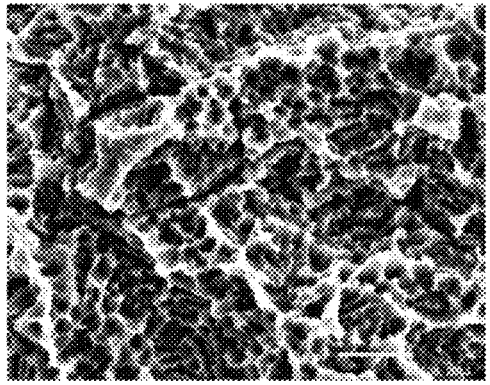
Figure 19:
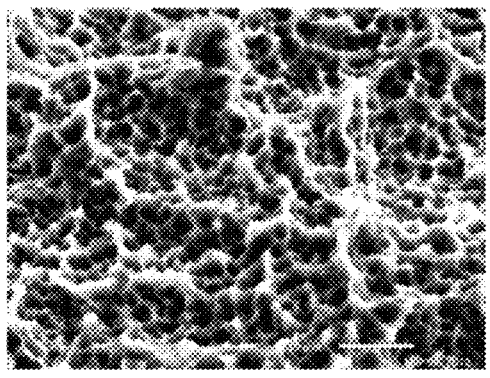

FIG. 19 presents referential images of outer surfaces of conventional titanium fixtures taken by SEM (magnification: 2,000 times), including (a) a product manufactured by Company A, (b) a product manufactured by Company B, (c) a product manufactured by Company C, and (d) a product manufactured by Company D.

As shown in FIG. 19, the outer surface of the conventional fixture is roughened (porosified). These outer surfaces are roughened by etching treatment with hydrochloric acid or the like, or blasting treatment. These outer surfaces have numerous pores and furthermore have numerous protrusions with pointed tips around the pores. The outer surfaces of the conventional fixtures have three-dimensional roughnesses Sa of 2 μm or more.

However, there is no protrusion (microvillus) with a hemispherical (fingertip-shaped) tip on any of the outer surfaces of the conventional fixtures, and the surfaces cannot be considered as microvillus-dense surfaces.

[Abutment 20]

The abutment (implant) 20 is a shaft-shaped member and is formed of a zirconia-containing ceramic.

The abutment 20 has a body section 23 and a tapered shaft section 25. The tapered shaft section 25 is fitted into a central hole of the fixture 10, and the body section 23 is disposed so as to be exposed from the tip side of the fixture 10.

The body section 23 is formed in a frustoconical shape or the like, to which the crown 6 is attached with an adhesive, cement, or the like. In the body section 23, the end side of the abutment 20 opposite to the crown 6 (a region not covered with the crown 6) is called a gingival margin 24. The gingival margin 24 is exposed between the fixture 10 and the crown 6.

The abutment 20 has the biological tissue rootage face 30 (biological tissue rootage faces 31 to 35). The biological tissue rootage face 30 is formed on an outer surface 21 of the abutment 20. The biological tissue rootage face 30 is formed on a gingival margin face (gingival margin 24).

Like the tip face 13 of the fixture 10, the gingival margin 24 is closely bonded to the gum S. For this reason, the biological tissue rootage face 30 (biological tissue rootage faces 31 to 35) is provided on the gingival margin 24 to facilitate adhesion of the gum S. Thereby, fusion of the abutment 20 with the gum S becomes firm compared to before.

The fixture 10 (10A, 10B) has a biological tissue rootage face 30 (biological tissue rootage faces 31 to 35) on the outer surface 11. This can enhance fixation (adhesion) of preosteoblasts and osteoblasts to the outer surface 11.

Since the biological tissue rootage face 30 has numerous microvilli 41, the surface area of the outer surface 11 is increased. The area in contact with blood is significantly increased, and the preosteoblasts and osteoblasts easily enter the outer surface 11. In particular, since the tip of the microvillus 41 is not pointed but is fingertip-shaped, the preosteoblasts and osteoblasts can smoothly enter the outer surface 11. Thus, the osteoblasts proliferate, resulting in firm osseointegration.

The biological tissue rootage face 30 (biological tissue rootage faces 31 to 35) has numerous small grooves 43 and large grooves 45. This can enhance proliferation of the osteoblasts.

Since aspects (number, shape, arrangement) of the small grooves 43 and the large grooves 45 can be variously set, a mechanical stimulation (mechanical stress) can be effectively applied to the preosteoblasts. Consequently, differentiation into osteoblasts is enhanced, and the duration of osseointegration is shortened.

In particular, the biological tissue rootage face 30 has a plurality of ups and downs with different sizes. The microvilli 41 form ups and downs in the order of nanometers. The small grooves 43 form ups and downs with a size of 1 to 9 micrometers. The large grooves 45 form ups and downs with sizes larger than those of the microvilli 41 and the small grooves 43. Thus, the biological tissue rootage face 30 can efficiently and effectively apply a mechanical stimulation to the preosteoblasts. Consequently, the bond between the fixture 10 and the alveolar bone H becomes firm compared to before, and the duration of osseointegration is also shortened.

Even if the fixture 10B does not have the male screw 15, the fixture 10B exerts the same action and effect as those of the fixture 10A. Since the biological tissue rootage face 30 exerts a high osseointegration performance, the fixture 10B can sufficiently bond to the alveolar bone H.

The abutment 20 has a biological tissue rootage face 30 (biological tissue rootage faces 31 to 35) on the outer surface 21 (gingival margin 24). Since the biological tissue rootage face 30 has numerous microvilli 41, conglutination property with the gingiva (conglutination property with the soft tissues) can be enhanced to prevent (block) bacterial invasion.

For the dental implant 1 (10A, 10B), the biological tissue rootage face 30 is formed on the outer surface 11 of the fixture 10 and the outer surface 21 of the abutment 20 respectively, and therefore the bondability with the human body becomes more firm. The dental implant 1A and the dental implant 1B exert the same action and effect.

The biological tissue rootage face 30 is formed on regions closely bonding to (rooting into) the biological tissues on the outer surfaces 11 and 21. The biological tissue rootage face 30 may be formed on one region or plural regions, as long as the regions are closely bonded to the biological tissues. The biological tissue rootage face 30 may have any area.

The biological tissue rootage face 30 may be formed on substantially the entire outer surfaces 11 and 21.

The biological tissue rootage face 30 may be formed over the entire face of regions to be closely bonded to the alveolar bone H (collar face 12, outer peripheral face 14, male screw 15) on the outer surface 11. The biological tissue rootage face 30 may be formed over the entire face of regions to be closely bonded to the gum S (tip face 13) on the outer surface 11.

The biological tissue rootage face 30 may be formed only on the outer surface 11, or only on the outer surface 21.

The biological tissue rootage faces 30 on the collar face 12, the tip face 13, the outer peripheral face 14 and the male screw 15 may have different surface properties (surface roughnesses). This is because the alveolar bone H is bonded to the collar face 12 and the male screw 15, and the gum S is conglutinated to the tip face 13.

The biological tissue rootage face 30 of the gingival margin 24 may be formed so as to have the same surface property (surface roughness) as that of the biological tissue rootage face 30 of the tip face 13. This is because the both biological tissue rootage faces 30 are conglutinated to the gum S.

The small grooves 43 and the large grooves 45 are formed so as to have semicircular cross sections. The cross-sectional shapes may be e.g. a triangle (isosceles triangle), a rectangle, or the like.

Each of the small groove 43 and large groove 45 may have a uniform width in the extending direction, or may have different widths, and furthermore may have a uniform depth in the extending direction, or may have different depths.

Each of the plural small grooves 43 and large grooves 45 may have a uniform width, or may have different widths, and furthermore may have a uniform depth, or may have different depths.

The numbers of the small grooves 43 and large grooves 45 are arbitrary. The small grooves 43 and large grooves 45 may be formed not only in a straight line but also in a curve line. Preferably, the adjacent small grooves 43 and the adjacent large grooves 45 are arranged at an interval as small as possible.

The extending direction of the small grooves 43 and the large grooves 45 forms any angle with respect to the vertical direction of the fixture 10.

The biological tissue rootage face 30 (biological tissue rootage faces 31 to 35) may be formed on both the outer surfaces 11 and 21. It is sufficient that any one or more of the biological tissue activation surfaces 31 to 35.

For the biological tissue rootage face 30, the numbers, shapes and arrangements of the small grooves 43 and the large grooves 45 can be arbitrarily set. The small grooves 43 and the large grooves 45 may have shapes other than the shapes for the biological tissue rootage faces 31 to 35.

The plurality of large grooves 45 may be arranged in a lattice pattern, on which furthermore the plurality of small grooves 43 may be arranged in a lattice pattern (the large grooves 45 and the small grooves 43 intersect each other and are superposed with each other).

The plurality of large grooves 45 may be arranged in parallel, on which furthermore the plurality of small grooves 43 may be arranged in a lattice pattern (the large grooves 45 and the small grooves 43 intersect each other and are superposed with each other).

Only the plurality of small grooves 43 may be arranged in a lattice pattern.

The biological tissue rootage face 30 may have only numerous microvilli 41 and no small grooves 43 and large grooves 45 (see a biological tissue rootage face 131 of the third embodiment).

[Method for Producing Dental Implant 1, and Method for Forming Biological Tissue Rootage Face 30]

The dental implant 1 (1A, 1B) is formed from a biocompatible ceramic material. The fixture 10 (10A, 10B) and the abutment 20 are formed from a zirconium oxide-containing ceramic material.

The manufacturing process for the fixture 10 (10A, 10B) includes a molding step, a sintering step, and a surface processing step. The surface processing step is a step of forming a biological tissue rootage face including a laser nonthermal processing step.

Since the manufacturing process for the abutment 20 is the same as the manufacturing process for the fixture 10, the explanation thereof is omitted.

(Molding Step and Sintering Step)

First, in the molding step, a pellet containing a zirconia powder is injection-molded to obtain a zirconia compact (ceramic compact).

Next, in the sintering step, the zirconia compact is subjected to presintering and main sintering to obtain a zirconia sintered compact (ceramic sintered compact).

(Surface processing step: laser nonthermal processing step)

Next, in the surface processing step, the outer surface 11 of the zirconia sintered compact is irradiated with a laser beam to form the biological tissue rootage face 30 (biological tissue rootage faces 31 to 35) on the outer surface 11.

For the laser beam, a laser beam of an ultrashort pulse laser is used. A laser beam of a picosecond laser or a femtosecond laser can be used.

The ultrashort pulse laser is an extremely short pulse laser with a pulse width (time width) ranging several picoseconds to several femtoseconds. A several-picosecond laser is a laser with a pulse width of one trillionth of a second. A femtosecond laser is a laser with a pulse width of one-quadrillionth of a second.

When the outer surface 11 of the zirconia sintered compact is irradiated with a laser beam of a femtosecond laser or the like, the outer surface 11 is non-thermally processed (laser nonthermal processing).

The nonthermal processing refers to a process that the sintered compact is irradiated with a laser beam under atmospheric pressure (in air containing moisture) to instantaneously melt, evaporate and scatter the sintered compact. Since the melted site is instantaneously evaporated, scattered and removed, thermal influence (thermal damage) to the surroundings of the processed portion is extremely small. For the nonthermal processing, a pulsed laser with a high laser beam output (peak power or energy density) is used.

The outer surface 11 is non-thermally processed with a laser beam to form the biological tissue rootage face 30 having numerous microvilli 41. The morphology such as the number and shape (size) of the microvilli 41 can be changed by adjusting the output and the like of the laser beam.

The small grooves 43 and the large grooves 45 are dug into the outer surface 11 by scanning the surface while emitting the laser beam. The plurality of small grooves 43 and large grooves 45 are formed by multiple scannings with the laser beam.

The machining width (light diameter) of the laser beam can be changed by adjusting the output of the laser beam. The widths and the depths of the small grooves 43 and large grooves 45 can be changed by adjusting the output (machining width) of the laser beam. Also, the widths and the depths of the small grooves 43 and large grooves 45 can be changed depending on the number of irradiation on the same portion, the scanning speed, the laser beam output, and the like.

When the small grooves 43 and the large grooves 45 are individually formed, first, the large grooves 45 are arranged, and then the small grooves 43 are formed.

When the small grooves 43 are arranged, or the large grooves 45 are arranged, or the small grooves 43 and the large grooves 45 are formed in a lattice pattern, scanning is carried out with a laser beam in two intersecting (orthogonal) directions. At this time, the intersection angle on the scanning is an intersection angle between the small grooves 43, between the large grooves 45, or between the small grooves 43 and the large grooves 45.

When the outer surface 11 is scraped with a laser beam to form the large grooves 45 and the small grooves 43, numerous microvilli 41 are simultaneously formed on the inner surfaces of the large grooves 45 and the small grooves 43. When the outer surface 11 is non-thermally processed with laser, the microvilli 41, the small grooves 43, and the large grooves 45 are formed at the same time to form the biological tissue rootage face 30 (biological tissue rootage faces 31 to 35).

In the surface processing step, the laser nonthermal processings on the collar face 12, the tip face 13, and the male screw 15 may be carried out with different laser beam outputs. Thereby, the collar face 12, the tip face 13, and the male screw 15 have different surface properties (surface roughnesses) of the biological tissue rootage face 30. This is because the alveolar bone H is bonded to the collar face 12 and the male screw 15, and the gum S is conglutinated to the tip face 13.

The formation of the biological tissue rootage face 30 (biological tissue rootage faces 31 to 35) is followed by cleaning, sterilization and the like.

In this way, the fixture 10 is produced.

The surface processing step (formation of the biological tissue rootage face) is not necessarily carried out after the main sintering of the fixture 10.

The presintering of the zirconia compact may be followed by the surface processing step of the zirconia sintered compact, and then the main sintering. Through this main sintering, the zirconia sintered compact contracts, and also the microvilli 41, the small grooves 43, and the large grooves 45 become small. Thus, in consideration of the contraction of the zirconia sintered compact, the biological tissue rootage face 30 is formed larger. Thereby, a fixture 10 (biological tissue rootage face 30) having the same shape as in the case of formation after the main sintering can be obtained.

The small grooves 43 and the large grooves 45 are not necessarily formed by the laser nonthermal processing. The small grooves 43 and the large grooves 45 may be formed on the outer surface 11 during the molding step. The small grooves 43 and the large grooves 45 may be formed by thermally processing the outer surface 11 with laser prior to the laser nonthermal processing.

As described above, the biological tissue rootage face 30 (biological tissue rootage faces 31 to 35) can be formed on the zirconium fixture 10 or the like by the laser nonthermal processing.

[Dental Implant 3 and Fixture 50]

Figure 10:
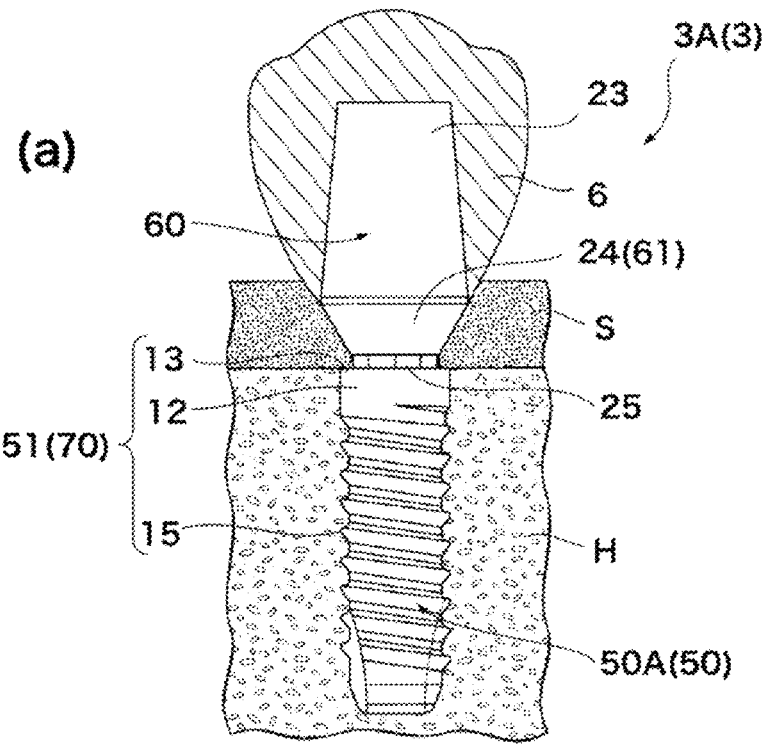
FIG. 10 presents drawings of a dental implant 3 according to the second embodiment of the present invention, including (a) screw-type dental implant 3A and (b) cylinder-type dental implant 3B.
Figure 10:
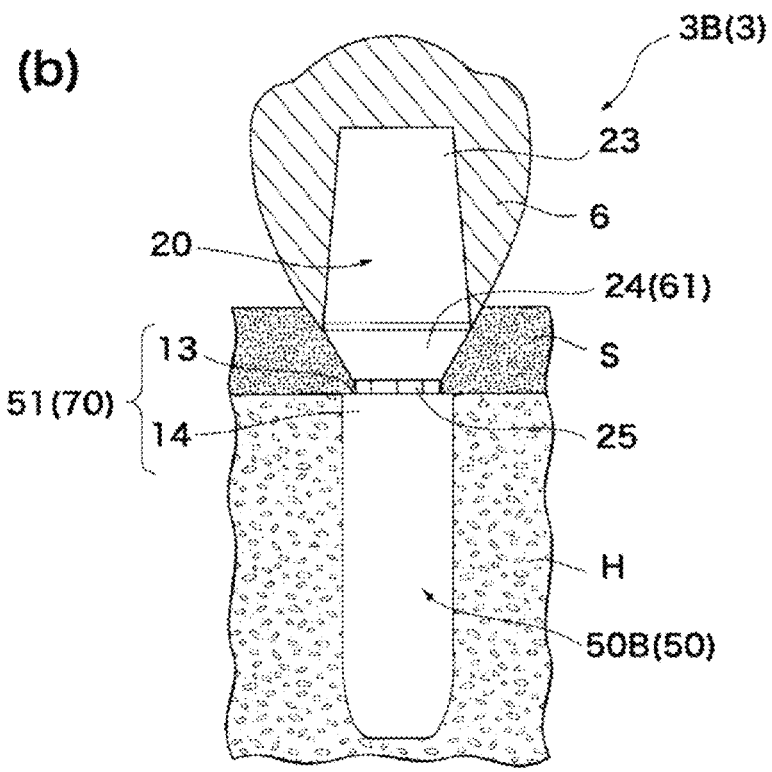

FIG. 10 presents drawings of a dental implant 3 according to the second embodiment of the present invention, including (a) screw-type dental implant 3A and (b) cylinder-type dental implant 3B.

The same symbols are attached to members and the like having the same shapes as of the members of the first embodiment, and the explanation therefor is omitted.

The dental implant 3 is a metal (titanium alloy) implant. The dental implant 3 includes the screw-type dental implant 3A and the cylinder-type dental implant 3B.

The dental implant 3 has a fixture 50 fixed to the alveolar bone H and an abutment 60 fitted into the fixture 50.

The fixture (implant) 50 is a shaft-shaped member having a central hole (not illustrated in the figures) and is formed of a titanium alloy (biocompatible material, biocompatible metallic material).

The fixture 50 is different from the fixture 10 only in the materials.

The fixture 50 includes a screw-type fixture 50A having a male screw 15 formed on an outer surface 51, and a cylinder-type fixture 50B having no male screw 15. The screw-type fixture 50A is different from the cylinder-type fixture 50B only in the presence of the male screw 15.

[Biological Tissue Rootage Face 70]

The fixture 50 has a biological tissue rootage face 70 (biological tissue rootage face 71). The biological tissue rootage face 70 is formed on the outer surface 51 of the fixture 50.

In the fixture 50A, the outer surface 51 includes the tip face 13, the collar face 12, and the screw face (male screw 15).

In the fixture 50B, the outer surface 51 includes the tip face 13 and the outer peripheral face 14.

Like the biological tissue rootage face 30, the biological tissue rootage face 70 is excellent in the bondability with the alveolar bone H and conglutination property with the gum S.

The biological tissue rootage face 70 has numerous microvilli 81 described later. The microvilli 81 are crowded. Like the biological tissue rootage face 30, the biological tissue rootage face 70 is a face with dense microvilli.

The biological tissue rootage face 70 may have either or both of small grooves 83 and large grooves 85 described later in addition to the microvilli 81.

The biological tissue rootage face 70 is different from the biological tissue rootage face 30 only in the materials. The microvilli 81 correspond to the microvilli 41, the small grooves 83 to the small grooves 43, and the large grooves 85 to the large grooves 45.

(Biological Tissue Activation Surface 71)

Figure 11:
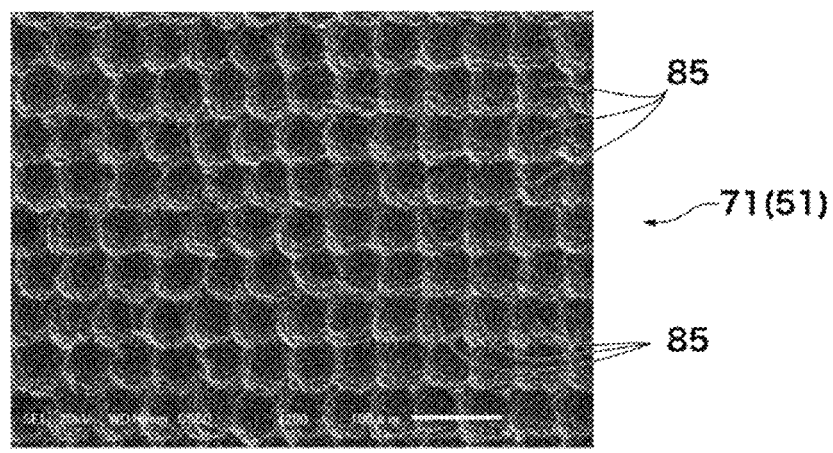
FIG. 11 presents images of a biological tissue rootage face 70 (biological tissue rootage face 71) according to the second embodiment of the present invention taken by SEM, including (a) an image at a magnification of 200 times, (b) an image at a magnification of 500 times, and (c) an image at a magnification of 2,000 times.
Figure 11:
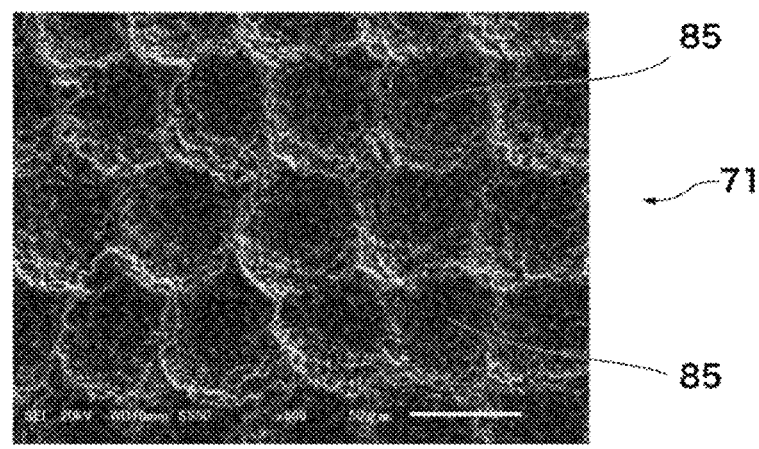
Figure 11:
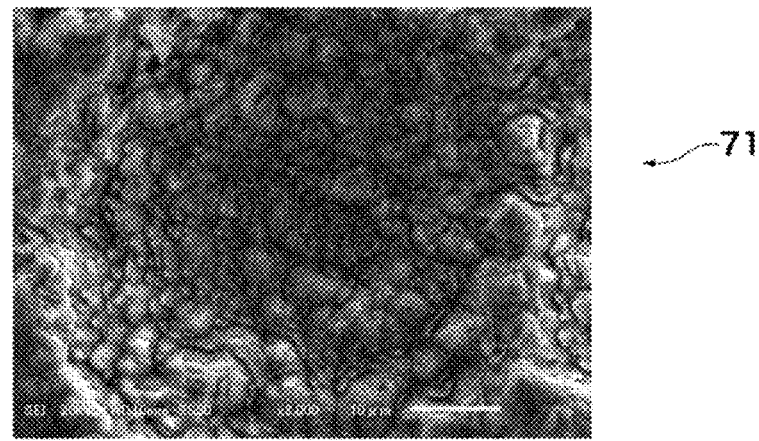
Figure 12:
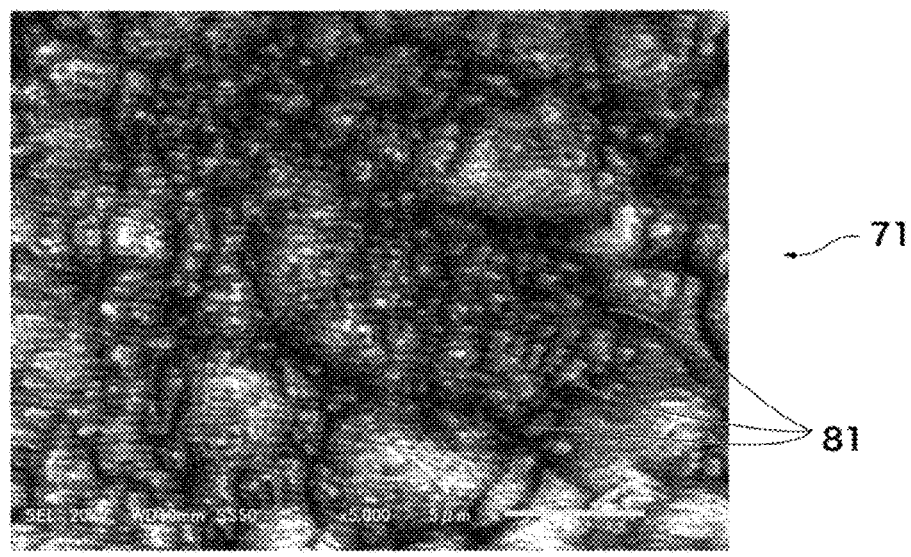
FIG. 12 presents images of a biological tissue rootage face 70 (biological tissue rootage face 71) according to the second embodiment of the present invention taken by SEM, including (d) an image at a magnification of 5,000 times, and (e) an image at a magnification of 10,000 times.
Figure 12:
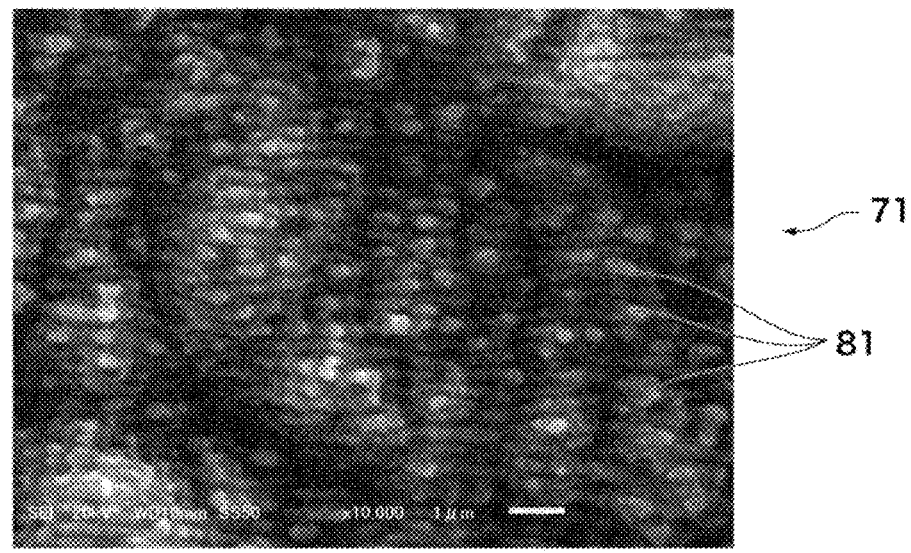

FIGS. 11 and 12 present images of the biological tissue rootage face 70 (biological tissue rootage face 71) according to the second embodiment of the present invention taken by SEM, including (a) an image at a magnification of 200 times, (b) an image at a magnification of 500 times, (c) an image at a magnification of 2,000 times, (d) an image at a magnification of 5,000 times, and (e) an image at a magnification of 10,000 times.

The biological tissue rootage face 71 is an example of the biological tissue rootage face 70 and has numerous microvilli 81. The shape and the like of the microvilli 81 are the same as those of the microvilli 41.

The biological tissue rootage face 71 has the same three-dimensional surface roughness Sa and interface developed area ratio Sdr as those of the biological tissue rootage face 30.

The biological tissue rootage face 71 has the plurality of large grooves 85 arranged so as to intersect with each other. The plurality of large grooves 85 are arranged in a lattice pattern. The number, shape and the like of the large grooves 85 are the same as those of the large grooves 45. The biological tissue rootage face 71 has the same morphology as of the biological tissue rootage face 31.

As another example of the biological tissue rootage face 70, a face with the same morphology as those of the biological tissue rootage faces 32 to 35 may be formed. The number, shape and the like of the small grooves 83 are the same as those of the small grooves 43.

The biological tissue rootage face 70 may have only numerous microvilli 81 and no small grooves 83 and no large grooves 85 (see the biological tissue rootage face 131 of the third embodiment).

[Abutment 60]

The abutment (implant) 60 is formed of a titanium alloy.

The abutment 60 has the biological tissue rootage face 70 (biological tissue rootage face 71). The biological tissue rootage face 70 is formed on an outer surface 61 of the abutment 60. The biological tissue rootage face 70 is formed on the gingival margin face (gingival margin 24).

The abutment 60 is different from the abutment 20 only in the materials.

The fixture 50 (50A, 50B) and the abutment 60 exert the same action and effect as those of the fixture 10 (10A, 10B) and the abutment 20.

In particular, the biological tissue rootage face 70 exerts the same action and effect as those of the biological tissue rootage face 30. The biological tissue rootage face 70 improves the ability of rooting into the biological tissue (bondability with hard tissues, and conglutination property with soft tissue) to accelerate the biological tissue fusion.

Consequently, the dental implant 3 (3A, 3B) exerts the same action and effect as those of the dental implant 1 (1A, 1B).

[Method for Producing Dental Implant 3, Method for Forming Biological Tissue Rootage Face 70]

The dental implant 3 (3A, 3B) is formed from a biocompatible metallic material. The fixture 50 (50A, 50B) and the abutment 60 are formed from a titanium alloy material.

The process for the fixture 50 (50A, 50B) includes a machining step and a surface processing step. The surface processing step is a step of forming the biological tissue rootage face and includes an acid etching step and a laser nonthermal processing step.

Since the manufacturing process for the abutment 60 is the same as the manufacturing process for the fixture 50, the explanation is omitted.

(Machining Step)

In the machining step, the titanium alloy material is cut using a combined lathe or the like or plastically processed to form a titanium workpiece (metal workpiece).

The outer surface 51 of the titanium workpiece is blasted. This is because the efficiency of the subsequent acid etching is improved. The blasting treatment on the titanium workpiece is arbitrarily carried out.

After the machining, the titanium workpiece is washed with water or alcohol.

(Surface Processing Step: Acid Etching Step)

In the surface processing step, first, the outer surface 51 of the titanium workpiece is acid-etched.

The titanium workpiece is etched by immersing it in hydrochloric acid. The concentration of the hydrochloric acid is e.g. 1% to 20%, the liquid temperature is e.g. 30° C. to 80° C., and the immersion time is e.g. 10 minutes to 60 minutes. The acid used for the etching may be an acid other than hydrochloric acid. Sulfuric acid, hydrofluoric acid, nitric acid, etc., and mixed acids thereof can be used.

After the acid etching step, the titanium workpiece is ultrasonically washed with pure water.

Figure 13:
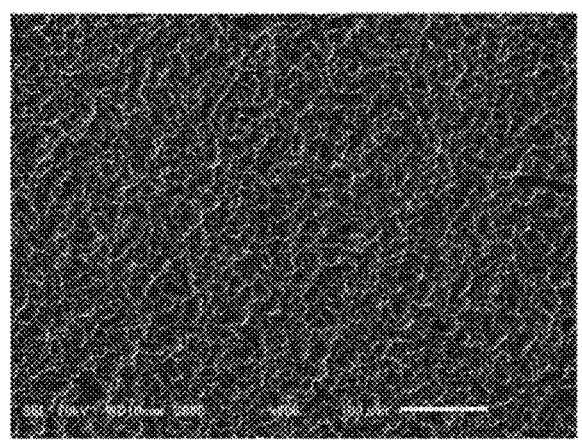
FIG. 13 presents images of an outer surface 51 of an acid-etched titanium workpiece taken by SEM, including (a) an image at a magnification of 200 times, (b) an image at a magnification of 500 times, and (c) an image at a magnification of 2,000 times.
Figure 13:
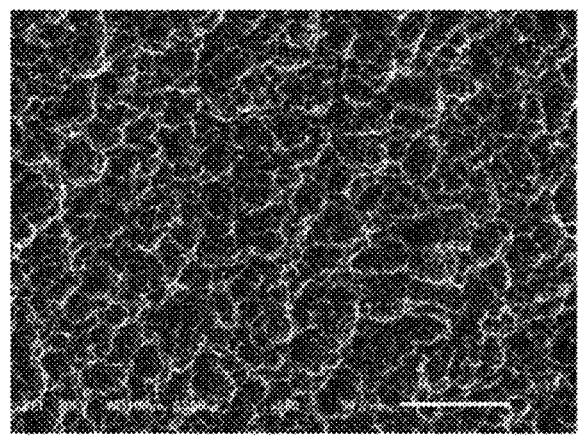
Figure 13:
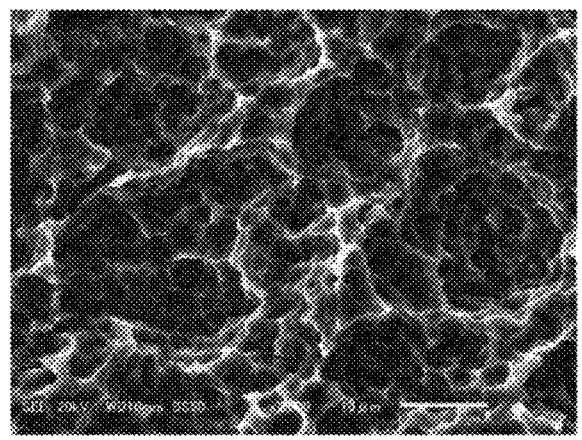
Figure 14:
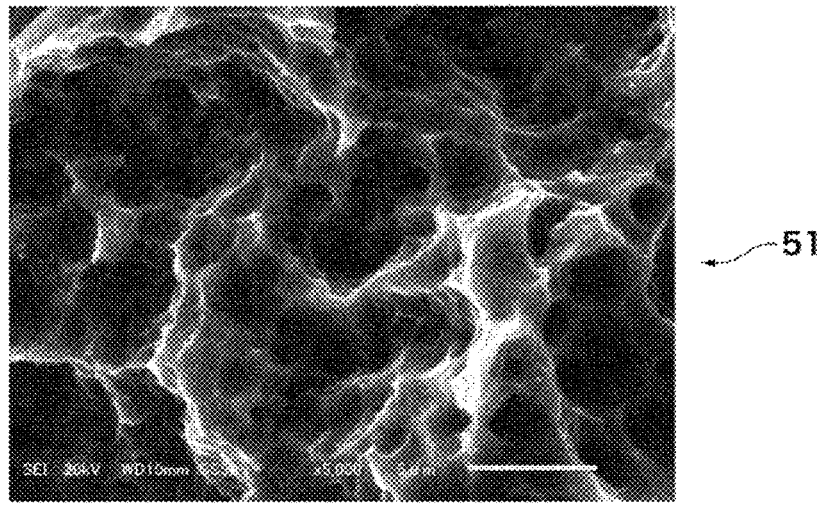
FIG. 14 presents images of the outer surface 51 of the acid-etched titanium workpiece taken by SEM, including (d) an image at a magnification of 5,000 times, and (e) an image at a magnification of 10,000 times.
Figure 14:
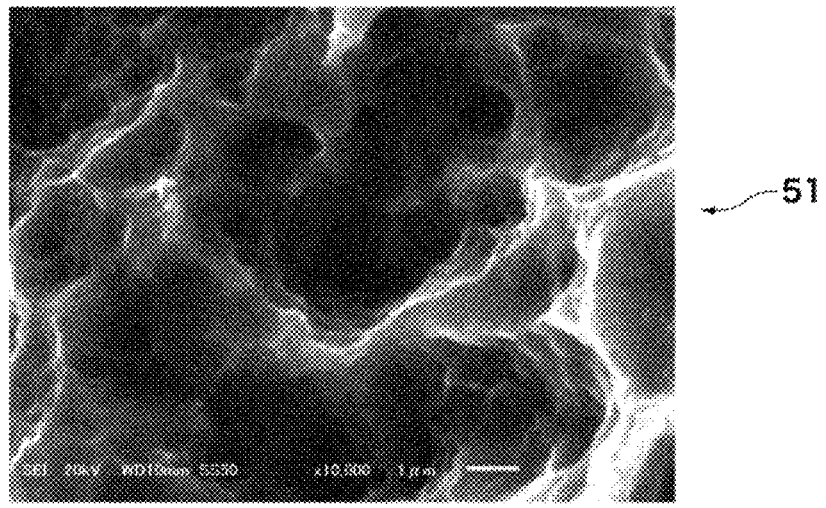

FIGS. 13 and 14 present images of the outer surface 51 of the acid-etched titanium workpiece taken by SEM, including (a) an image at a magnification of 200 times, (b) an image at a magnification of 500 times, (c) an image at a magnification of 2,000 times, (d) an image at a magnification of 5,000 times, and (e) an image at a magnification of 10,000 times.

FIGS. 13 and 14 present images of the outer surface 51 of the acid-etched titanium workpiece taken by SEM, including (a) an image at a magnification of 200 times, (b) an image at a magnification of 500 times, (c) an image at a magnification of 2,000 times, (d) an image at a magnification of 5,000 times, and (e) an image at a magnification of 10,000 times.

The outer surface 51 of the acid-etched titanium workpiece (acid-etched metal workpiece) has numerous pores and furthermore has numerous protrusions having pointed tips around the pores. This outer surface 51 is rough (porous), and is the same as the outer surface of the conventional fixture (see FIG. 19).

On this outer surface 51, there is no microvillus 41 yet.

(Surface Processing Step: Laser Nonthermal Processing Step)

Next, the outer surface 51 of the titanium workpiece is irradiated with laser beam to form a biological tissue rootage face 70 (biological tissue rootage face 71) on the outer surface 51.

This laser nonthermal processing step is the same as the laser nonthermal processing step of the biological tissue rootage face 30.

When the outer surface 51 of the acid etched titanium workpiece is irradiated with a laser beam of a femtosecond laser or the like, the outer surface 51 is non-thermally processed (laser nonthermal processing). The outer surface 51 is non-thermally processed with a laser beam to form the numerous microvilli 81.

The small grooves 83 and the large grooves 85 are dug into the outer surface 51 by scanning the surface while emitting the laser beam. When the outer surface 51 is non-thermally processed with laser, the microvilli 81, the small grooves 83, and the large grooves 85 are formed at the same time to form the biological tissue rootage face 70 (biological tissue rootage face 71).

The formation of the biological tissue rootage face 70 (biological tissue rootage face 71) is followed by cleaning, sterilization and the like.

In this way, the fixture 50 is produced.

The small grooves 83 and the large grooves 85 are not necessarily formed by the laser nonthermal processing. The small grooves 83 and the large grooves 85 may be formed on the outer surface 51 in the machining step. The small grooves 83 and the large grooves 85 may be formed by thermally processing the outer surface 51 with laser prior to the laser nonthermal processing.

As described above, the biological tissue rootage face 70 (biological tissue rootage face 71) can be formed on the titanium alloy fixture 50 or the like by the acid etching and the laser nonthermal processing.

[Hip Prosthesis 101, Stem 103]

Figure 15:
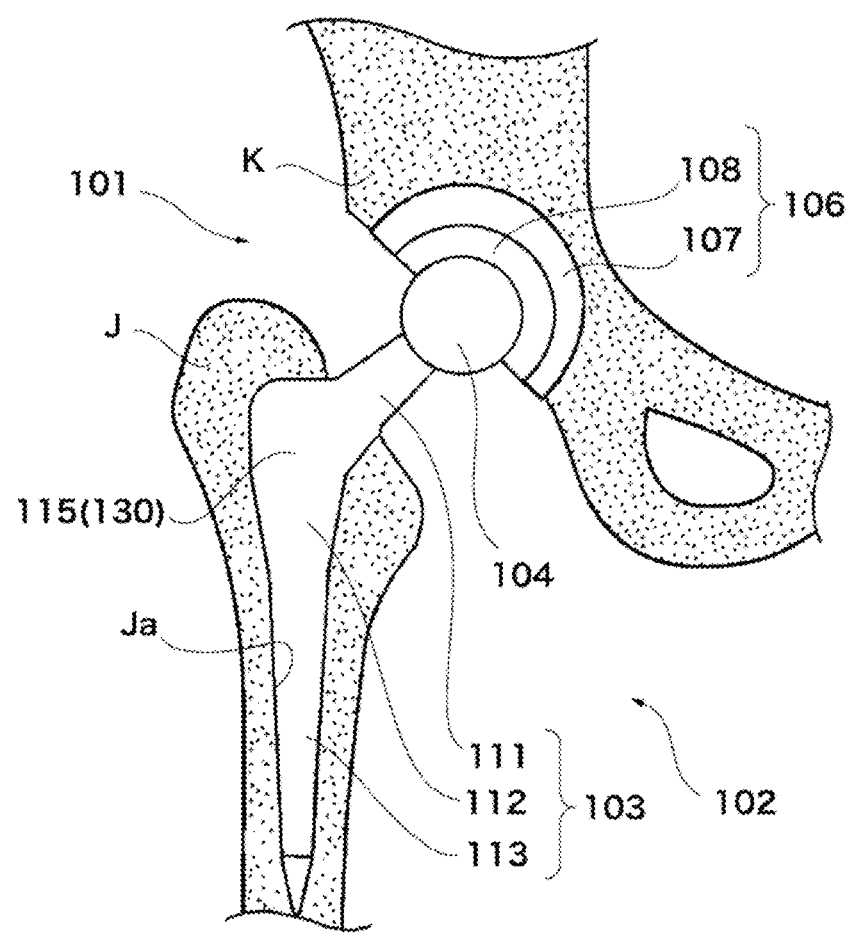
FIG. 15 presents a drawing of a hip prosthesis 101 according to the third embodiment of the present invention.

FIG. 15 presents a drawing of a hip prosthesis 101 according to the third embodiment of the present invention.

When a hip joint is damaged, the hip prosthesis 101 replaces the hip joint to restore the function of the hip joint. The hip prosthesis 101 is composed of a femoral component 102 implanted in a femur J and an acetabular component 106 implanted in an acetabulum K.

The femoral component 102 comprises a stem 103 and a head 104.

The stem 103 is implanted in the femur J (biological tissue, hard tissue) to support the head 104.

The head 104 is a spherical member playing a role of an epiphysis of the femur J and is formed of a biocompatible ceramic material such as zirconia.

The acetabular component 106 comprises a cup 107 and a liner 108.

The cup 107 is a bowl-shaped member implanted in an acetabulum K (biological tissue, hard tissue) and is formed of a biocompatible ceramic material such as zirconia or a biocompatible metallic material such as a titanium alloy. The biological tissue rootage faces 30 and 70 may be formed on the outer surface of the cup 107.

The liner 108 is a bowl-shaped member fixed inside the cup 107 and is formed of e.g. an ultrahigh molecular weight polyethylene resin. The liner 108 slidably supports the head 104 and plays a role of an articular surface.

An extending direction of the femoral component 102 is referred to as the vertical direction. In the vertical direction, the side of the head 104 is referred to as a tip (first end), and the side of the stem 103 is referred to as a distal end (second end). The width direction of the stem 103 is referred to as a lateral direction. The thickness direction of the stem 103 is referred to as an anteroposterior direction.

The stem (implant) 103 is inserted into a narrowing hole Ja formed in the femur J and osteointegrated. The stem 103 supports the head 104 and transmits a load to the femur J.

The stem 103 is formed of a biocompatible resin material (biocompatible material). The stem 103 is formed of a polyetheretherketone resin (PEKK: polyetherketoneketone).

The stem 103 has a body section 111, a leg section 112, and a neck section 113, which are integrally formed of a polyetheretherketone resin.

The body section 111 is a block-shaped portion extending in the vertical direction, inserted into the narrowing hole Ja, and osteointegrated.

The body section 111 has a length of about 50 mm in the vertical direction. The body section 111 has a width gradually narrowing from the tip toward the distal end. The tip side has a width of about 33 mm and the distal end side has a width of about 15 mm. The body section 111 has a thickness which is substantially constant from the tip side toward the distal end side. The tip side has a thickness of about 13 mm and the distal end side has a thickness of about 11 mm.

The leg section 112 is a substantially square pole-shaped portion extending in the vertical direction and is disposed on the end side of the body section 111. The leg section 112 guides the body section 111 into the narrowing hole Ja and holds the posture of the implanted stem 103.

The leg section 112 has a length of about 90 mm in the vertical direction. The leg section 112 gradually narrows from the tip toward the distal end.

The neck section 113 is a substantially cylindrical portion extending in the vertical direction and is disposed on the tip side of the body section 111. The neck section 113 protrudes from the narrowing hole Ja and introduces a load from the acetabulum side.

The neck section 113 has a length of about 22 mm. The neck section 113 gradually thickens from the tip toward the distal end. On the tip of the neck section 113, a head-joining section is formed.

[Biological Tissue Rootage Face 130]

The stem 103 has a biological tissue rootage face 130 (biological tissue rootage face 131). The biological tissue rootage face 130 is formed on an outer surface 115 of the sites implanted in the narrowing hole Ja (body section 111, leg section 112) on the outer surface of the stem 103. The biological tissue rootage face 130 is also formed on at least the outer surface 115 of the body section 111.

Like the biological tissue rootage faces 30 and 70, the biological tissue rootage face 130 is excellent in bondability with natural bones (femur J). The biological tissue rootage face 130 has numerous microvilli 141 described later. The microvilli 141 are crowded. Like the biological tissue rootage faces 30 and 70, the biological tissue rootage face 130 is a face with dense microvilli.

The biological tissue rootage face 130 has the microvilli 141 and may further have either or both of small grooves and large grooves.

The biological tissue rootage face 130 is different from the biological tissue rootage faces 30 and 70 only in the materials. The microvilli 141 corresponds to the microvilli 41 and 81, the small grooves correspond to the small grooves 43 and 83, and the large grooves correspond to the large grooves 45 and 85.

(Biological Tissue Rootage Face 131)

Figure 16:
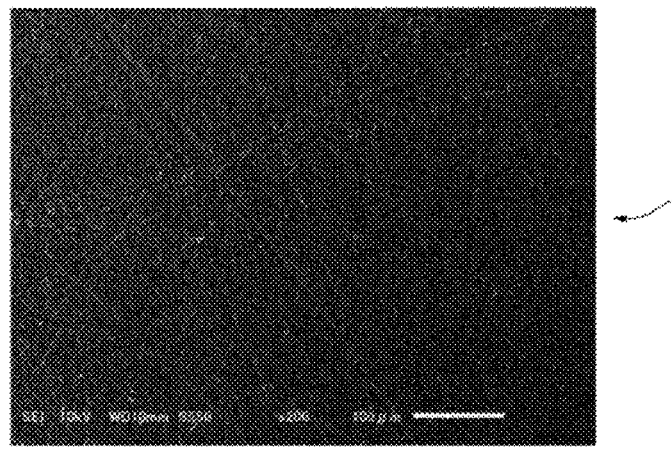
FIG. 16 presents images of a biological tissue rootage face 130 (biological tissue rootage face 131) according to the third embodiment of the present invention taken by SEM, including (a) an image at a magnification of 200 times, (b) an image at a magnification of 500 times, and (c) an image at a magnification of 2,000 times.
Figure 16:
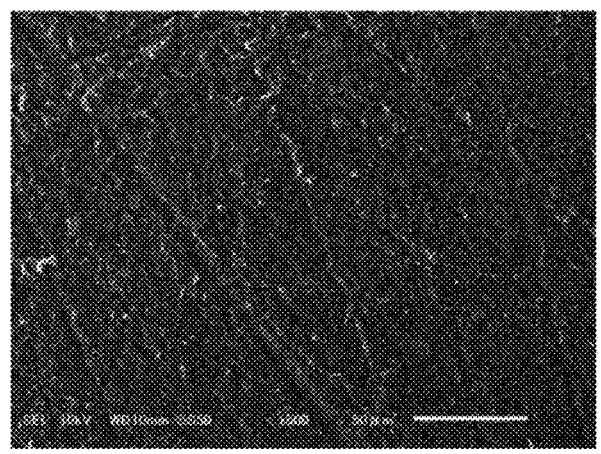
Figure 16:
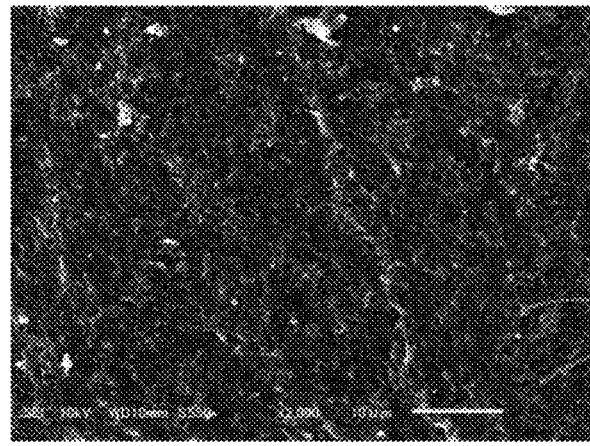
Figure 17:
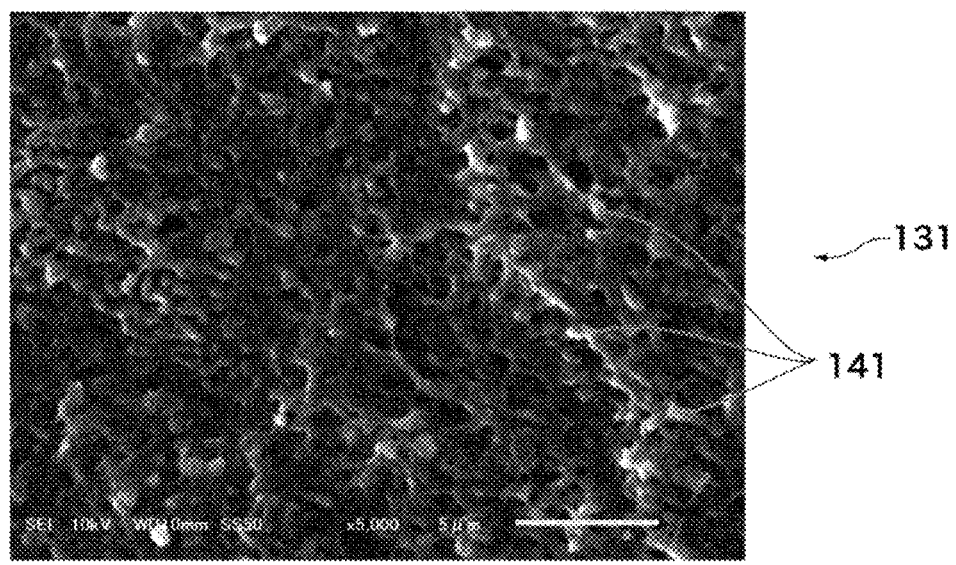
FIG. 17 presents images of the biological tissue rootage face 130 (biological tissue rootage face 131) according to the second embodiment of the present invention taken by SEM, including (d) an image at a magnification of 5,000 times, and (e) an image at a magnification of 10,000 times.
Figure 17:
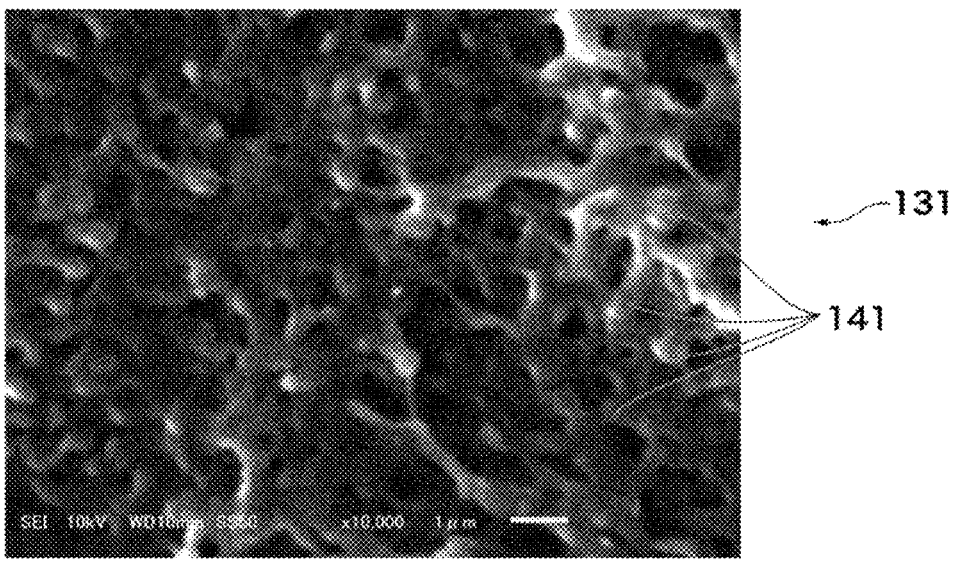

FIGS. 16 and 17 present images of a biological tissue rootage face 130 (biological tissue rootage face 131) according to the third embodiment of the present invention taken by SEM, including (a) an image at a magnification of 200 times, (b) an image at a magnification of 500 times, (c) an image at a magnification of 2,000 times, (d) an image at a magnification of 5,000 times, and (e) an image at a magnification of 10,000 times.

The biological tissue rootage face 131 is an example of the biological tissue rootage face 130 and has numerous microvilli 141. The shape and the like of the microvilli 141 are the same as those of the microvilli 41 and 81.

The biological tissue rootage face 131 has the same three-dimensional surface roughness Sa and interface developed area ratio Sdr as those of the biological tissue rootage faces 30 and 70.

As another example of the biological tissue rootage face 130, a face having the same morphology as that of the biological tissue rootage faces 31 to 35, 71 and the like may be formed. The biological tissue rootage face 130 may have small grooves or large grooves. The small grooves and the large grooves correspond to the small grooves 43 and 83, and to the large grooves 45 and 85 respectively. The numbers, shapes and the like of the small grooves and the large grooves of the biological tissue rootage face 130 are the same as those of the small grooves 43 and 83 and the large grooves 45 and 85 respectively.

The stem 103 exerts the same action and effect as those of the fixtures 10 and 50. The biological tissue rootage face 130 exerts the same action and effect as those of the biological tissue rootage faces 30 and 70. The biological tissue rootage face 130 improves the ability of rooting into the biological tissue (bondability with hard tissues) to accelerate the biological tissue fusion.

Particularly, even if the biological tissue rootage face 130 is composed only of a resin face, the biological tissue rootage face 130 can exert the ability of rooting into the biological tissue. For this reason, it is unnecessary to coat the resin face with a metal or a ceramic, or to mix the resin material with a metal or a ceramic.

For the hip prosthesis 101, the biological tissue rootage face 130 is formed on the outer surface 115 of the stem 103, and therefore the bondability with the human body becomes firm.

Consequently, the hip prosthesis 101 exerts the same action and effect as those of the dental implants 1 and 3.

[Method for Producing Hip Prosthesis 101, and Method for Forming Biological Tissue Rootage Face 130]

The hip prosthesis 101 is formed from a biocompatible resin material. The stem 103 is formed from polyetheretherketone resin.

The manufacturing process for the stem 103 includes a molding step and a surface processing step. The surface processing step is a step of forming the biological tissue rootage face, and includes a laser nonthermal processing step.

Since the manufacturing processes of the head 104, the cup 107 and the liner 108 are the same as the conventional method, their explanation will be omitted.

(Molding Step)

In the molding step, a polyetheretherketone resin pellet is injection-molded to obtain a polyetheretherketone compact (resin compact).

(Surface Processing Step: Laser Nonthermal Processing Step)

Next, in the surface processing step, the outer surface 115 of the polyetheretherketone compact is irradiated with a laser beam to form the biological tissue rootage face 130 (biological tissue rootage face 131) on the outer surface 115.

This laser nonthermal processing step is the same as the laser nonthermal processing steps of the biological tissue rootage faces 30 and 70.

When the outer surface 115 of the polyetheretherketone compact is irradiated with a laser beam of a femtosecond laser or the like, the outer surface 115 is non-thermally processed (laser nonthermal processing). The outer surface 115 is non-thermally processed with a laser beam to form the biological tissue rootage face 131 having the numerous microvilli 141.

The small grooves and the large grooves may be formed on the outer surface 115 by scanning the surface while emitting the laser beam. When the outer surface 115 is non-thermally processed with laser, the microvilli 141, the small grooves and the large grooves are formed at the same time to form the biological tissue rootage face 130.

The formation of the biological tissue rootage face 130 (biological tissue rootage face 131) is followed by cleaning, sterilization and the like.

In this way, the stem 103 is produced.

The small grooves 83 and the large grooves 85 are not necessarily formed by the laser nonthermal processing. The small grooves 83 and the large grooves 85 may be formed on the outer surface 51 during the machining step. The small grooves 83 and the large grooves 85 may be formed by thermally processing the outer surface 51 with laser prior to the laser nonthermal processing.

The biological tissue rootage face 130 is formed on a region (outer surface 115) closely bonding to (rooting into) the femur J on the outer surface of the stem 103. The biological tissue rootage face 130 may be formed on one region or plural regions, as long as the regions are faces capable of closely bonding to the femur J. The biological tissue rootage face 130 may have any area.

The biological tissue rootage face 130 may be formed on substantially the entire outer surface 115.

The biological tissue rootage face 130 may be formed only on the outer surface of the body portion 111 (face excluding the outer surface of the leg section 112) on the outer surface 115.

As described above, the biological tissue rootage face 130 (biological tissue rootage face 131) can be formed on the stem 103 made of the polyetheretherketone resin by the laser nonthermal processing.

The stem 103 may be formed of not only the polyetheretherketone resin but also a biocompatible a biocompatible ceramic material such as zirconia or a biocompatible metallic material such as a titanium alloy. The biological tissue rootage faces 30 and 70 may be formed on the outer surface 115 of the stem 103.

[Animal Experiment]

Figure 18:
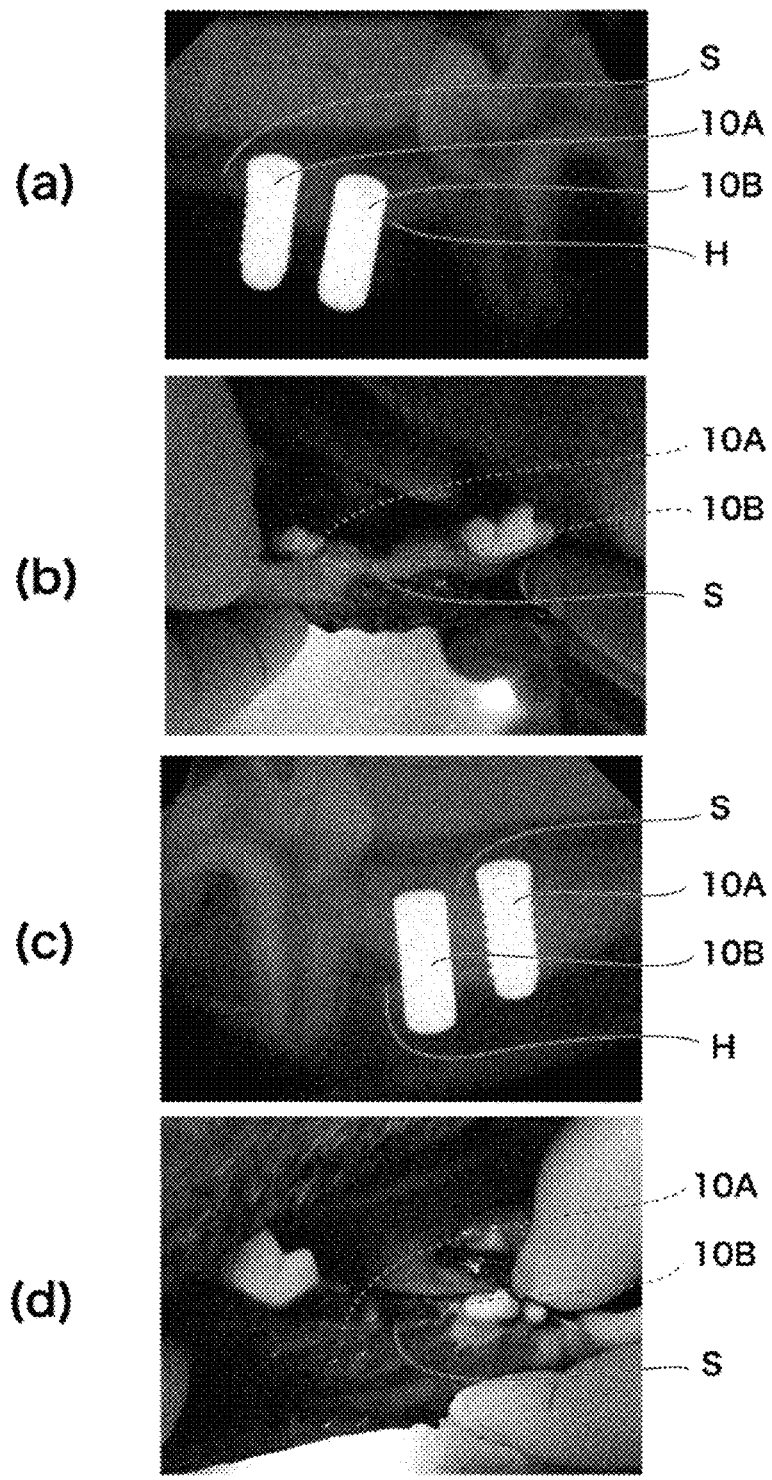
FIG. 18 presents images showing results of an animal experiment, including (a) an X-ray image of an alveolar bone H on a left mandible, (b) an image of a gum S on a right mandible, (c) an X-ray image of the alveolar bone H of the left mandible, and (d) an image of the gum S on the right mandible.

FIG. 18 presents images showing results of an animal experiment, including (a) an X-ray image of an alveolar bone H on a left mandible, (b) an image of a gum S on a right mandible, (c) an X-ray image of the alveolar bone H of the left mandible, and (d) an image of the gum S on the right mandible.

One fixture 10A and one fixture 10B were respectively implanted in the right and left alveolar bones H on the mandible of a dog. Four weeks after the implantation, a state of the fixture 10 was imaged with a roentgen device or the like.

As a result of the animal experiment, it was confirmed that the gum S (gingiva) did not have inflammation. Also, it was confirmed that the gum S did not contract and the alveolar bone H did not reduce.

The conglutination property of the fixture 10 (10A, 10B) with the gum S (conglutination property to soft tissues) could be improved to prevent (block) bacterial invasion.

The fixture (10A, 10B) was osteointegrated to the extent of not withdrawing them from the alveolar bone H by human power. The osseointegration of the fixture (10A, 10B) with the alveolar bone H (bondability with hard tissues) could be improved to shorten the duration of osseointegration.

In this manner, the rooting ability (bondability with hard tissues and conglutination property with soft tissues) of the fixture 10 (10A, 10B) could be improved to enhance (accelerate) the biological tissue fusion.

The present invention is not limited to the above-described embodiments but includes the embodiments with various modifications without departing from the purpose of the present invention. That is, the specific shapes, configurations and the like cited in the embodiments are merely examples, and can be appropriately changed.

In the above embodiments, the dental implants 1 and 3 to be implanted in the alveolar bone H, and the hip prosthesis 101 implanted in the femur J have been explained, but the present invention is not limited thereto.

The implant of the present invention may be an artificial bone, a bone prosthetic material, or the like. The artificial bone and the bone prosthetic material are used to compensate for a bone defective site due to fracture, tumor resection or the like, a cartilage removed by lumbar surgery, and the like.

The implant according to the present invention may be a member of an artificial joint, an osseointegration material used for fixing a fracture site, a fixture for a spine or the like (a spinal implant or a lumbar implant).

The implant is not necessarily implanted in a living body (in a body) but may be fixed to a body surface. The implant may be applied not only to humans but also pets, livestock, and the like.

The biological tissue rootage face may have ups and downs such as other grooves and ridges in addition to or instead of the small grooves and the large grooves.

In the above embodiments, although the case of zirconia (zirconium oxide) has been described for the biocompatible ceramic material, the material may be a combined material of zirconia with carbon, resin, glass or the like. It is sufficient that zirconia (zirconium oxide) is contained in a volume ratio of at least 50% relative to the implant. Zirconia (zirconium oxide) is contained in a volume ratio of 90% or more relative to the implant.

As the biocompatible ceramic material, alumina (aluminum oxide), yttrium oxide, hafnium oxide, silicone oxide, magnesium oxide, cerium oxide or the like may be adopted.

The biocompatible metallic material may be copper, titanium, a titanium alloy, a cobalt-chromium alloy, or the like. The biocompatible resin material may be silicon, nylon, POM, a composite material or the like.

REFERENCE NUMERALS 1, 1A, 1B, 3, 3A, 3B dental implant
10, 10A, 10B fixture (implant)
11 outer surface
12 collar face
13 tip face
14 outer peripheral face
15 male screw (screw face)
20 abutment (implant)
21 outer surface
24 gingival margin (gingival margin face)

30 (31, 32, 33, 34) biological tissue rootage face
41 microvilli
43 small groove (first groove)
45 large groove (second groove)
50, 50A, 50B fixture (implant)
60 abutment (implant)
70 (71) biological tissue rootage face
81 microvilli
83 small groove (first groove)
85 large groove (second groove)
101 hip prosthesis
103 stem (implant)
111 body section
112 leg section
115 outer surface
130, 131 biological tissue rootage face
141 microvilli
H alveolar bone (biological tissue, hard tissue)
S gum (biological tissue, soft tissue)
J femur (biological tissue, hard tissue)
K acetabulum (biological tissue, hard tissue)

What is claimed is:

1. A method for forming a biological tissue rootage face capable of rooting into a biological tissue, comprising
a first step of forming a large groove on a surface; and
a second step of forming a small groove on an inner surface of the large groove and simultaneously forming a rough surface on an inner surface of the small groove, the rough surface having numerous fingertip-shaped microvilli;
wherein the large groove is formed by molding, machining or laser thermal processing and the small groove and the rough surface are formed by laser nonthermal processing;
wherein each of the fingertip-shaped microvilli has a tip diameter of less than 1000 nanometers.

2. The method for forming the biological tissue rootage face according to claim 1,
wherein the laser nonthermal process uses an ultrashort pulse laser.

3. The method for forming the biological tissue rootage face according to claim 2,
wherein the ultrashort pulse laser is a picosecond laser or a femtosecond laser.

4. A method for producing an implant capable of rooting into a biological tissue, comprising a step of forming a surface capable of rooting to the biological tissue which includes the method for forming the biological tissue rootage face according to claim 1.

5. A method for forming a biological tissue rootage face capable of rooting into a biological tissue, comprising:
a step of subjecting a surface of a biocompatible material to a laser nonthermal process to form a groove and simultaneously forming a rough surface having numerous fingertip-shaped microvilli on an inner surface of the groove;
wherein each of the fingertip-shaped microvilli has a tip diameter of less than 1000 nanometers.

6. The method for forming the biological tissue rootage face according to claim 5, wherein the laser nonthermal process uses an ultrashort pulse laser.

7. The method for forming the biological tissue rootage face according to claim 6, wherein the ultrashort pulse laser is a picosecond laser or a femtosecond laser.

8. A method for producing an implant capable of rooting into a biological tissue, comprising a step of forming a surface capable of rooting to the biological tissue which includes the method for forming the biological tissue rootage face according to claim 5.

9. A method for forming a biological tissue rootage face capable of rooting into a biological tissue by subjecting a surface of a biocompatible material to laser nonthermal processing carried out by emitting a laser beam in air, comprising:
a first step of forming a large groove on the surface; and
a second step of forming a small groove on an inner surface of the large groove and simultaneously forming a rough surface on an inner surface of the small groove, the rough surface having numerous fingertip-shaped microvilli;
wherein each of the fingertip-shaped microvilli has a tip diameter of less than 1000 nanometers.

10. The method for forming the biological tissue rootage face according to claim 9, wherein the laser beam is a laser beam of an ultrashort pulse laser.

11. The method for forming the biological tissue rootage face according to claim 10, wherein the ultrashort pulse laser is a picosecond laser or a femtosecond laser.

12. A method for producing an implant capable of rooting into a biological tissue, comprising
a step of forming a surface capable of rooting to the biological tissue which includes the method for forming the biological tissue rootage face according to claim 9.

* * * * *